(12) United States Patent
Jia et al.

(10) Patent No.: US 12,385,084 B2
(45) Date of Patent: Aug. 12, 2025

(54) ENHANCING AGENT AND KIT FOR ENHANCING NUCLEIC ACID AMPLIFICATION REACTION AND METHOD FOR PERFORMING NUCLEIC ACID AMPLIFICATION REACTION

(71) Applicant: University of Macau, Macau (CN)

(72) Inventors: Yanwei Jia, Macau (CN); Ren Shen, Macau (CN); Pui-In Mak, Macau (CN); Rui Paulo da Silva Martins, Macau (CN)

(73) Assignee: University of Macau, Macau (CN)

( * ) Notice: Subject to any disclaimer, the term of this patent is extended or adjusted under 35 U.S.C. 154(b) by 0 days.

(21) Appl. No.: 16/792,626

(22) Filed: Feb. 17, 2020

(65) Prior Publication Data

US 2020/0362400 A1    Nov. 19, 2020

Related U.S. Application Data

(60) Provisional application No. 62/849,173, filed on May 17, 2019.

(30) Foreign Application Priority Data

Sep. 26, 2019 (CN) .......................... 201910916167.5

(51) Int. Cl.
 *C12Q 1/6848* (2018.01)
 *C12Q 1/686* (2018.01)

(52) U.S. Cl.
 CPC ........... *C12Q 1/6848* (2013.01); *C12Q 1/686* (2013.01); *C12Q 2531/113* (2013.01); *C12Q 2561/113* (2013.01)

(58) Field of Classification Search
 CPC .................. C12Q 1/6848; C12Q 1/686; C12Q 2531/113; C12Q 2561/113; C12Q 2563/107
See application file for complete search history.

(56) References Cited

U.S. PATENT DOCUMENTS 8,067,039 B2 *  11/2011  Wu .......................... A61P 27/02
                                                    424/725

FOREIGN PATENT DOCUMENTS

WO    WO-2007041201 A2 *  4/2007    ........... C12N 15/115

OTHER PUBLICATIONS

Xiang et al., "Highly sensitive fluorescence quantitative detection of specific DNA sequences with molecular beacons and nucleic acid dye SYBR Green I," Talanta, vol. 129, pp. 249-253. (Year: 2014).*
Fan et al., "A simple adenosine fluorescent aptasensor based on the quenching ability of guanine," New J. Chem., vol. 36, pp. 2260-2265. (Year: 2012).*

* cited by examiner

*Primary Examiner* — Young J Kim
(74) *Attorney, Agent, or Firm* — Davis Wright Tremaine LLP

(57) ABSTRACT

The present disclosure discloses an enhancing agent and a kit for enhancing nucleic acid amplification reaction and a method for performing nucleic acid amplification reaction, relating to the field of biotechnology. The enhancing agent disclosed in the present disclosure has a domain capable of binding to fluorescent dye and a quenching group for quenching fluorescence emitted by the fluorescent dye bound to the domain binds. As the binding affinity between the above domain and the fluorescent dye is lower than the binding affinity between a target amplification product of nucleic acid amplification reaction and the fluorescent dye, the enhancing agent not only can reduce inhibition of high-concentration fluorescent dye to amplification reaction, but also can enhance signal intensity of the fluorescent dye in the nucleic acid amplification reaction based on microfluidic chip, improving reliability of application of the fluorescent dye as amplification indicator on the microfluidic chip.

4 Claims, 13 Drawing Sheets

Specification includes a Sequence Listing.

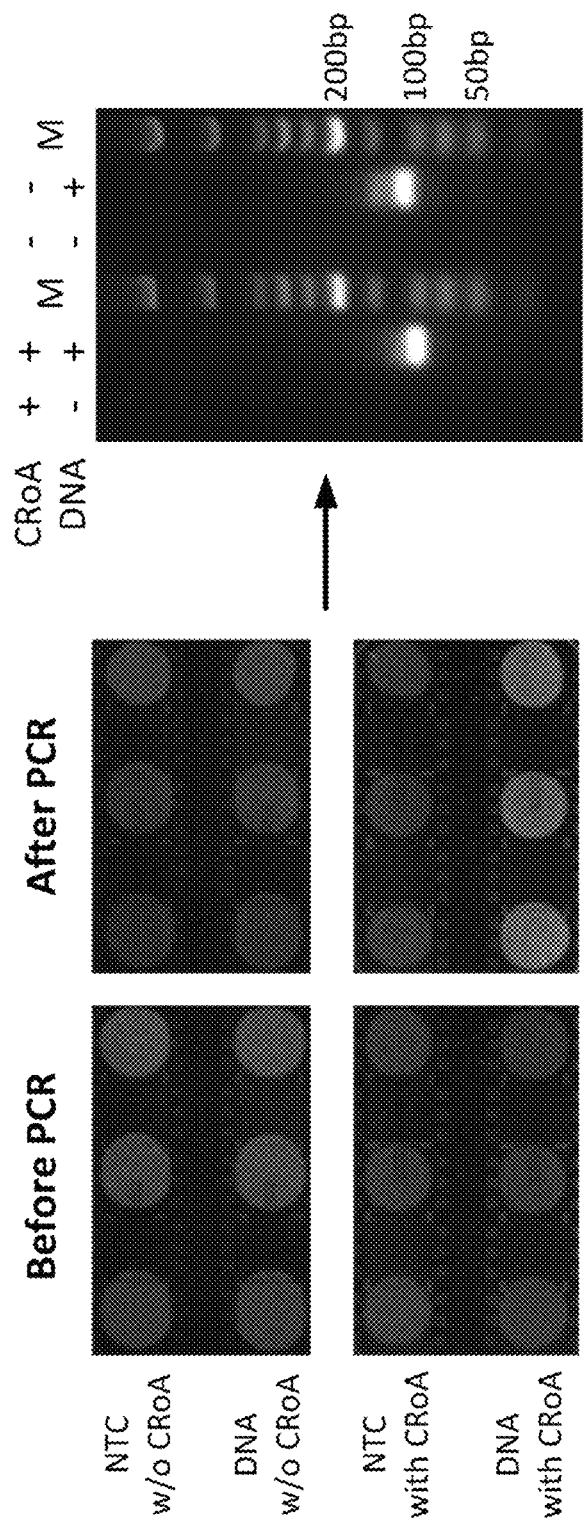

ENHANCING AGENT AND KIT FOR ENHANCING NUCLEIC ACID AMPLIFICATION REACTION AND METHOD FOR PERFORMING NUCLEIC ACID AMPLIFICATION REACTION

CROSS-REFERENCE TO RELATED APPLICATIONS

The present application claims the priority of the U.S. Provisional patent application No. 62/849,173, filed with the USPTO on May 17, 2019, and the priority of the Chinese patent application No. 201910916167.5, filed with the Chinese Patent Office on Sep. 26, 2019, and entitled "Enhancing Agent and Kit for Enhancing Nucleic Acid Amplification Reaction and Method for Performing Nucleic Acid Amplification Reaction" which are incorporated herein by reference in its entirety.

SEQUENCE LISTING

The application contains a Sequence Listing electronically submitted via EFS-web to the United States Patent and Trademark Office as a text file named "Sequence_Listing.txt." The electronically filed Sequence Listing serves as both the paper copy required by 37 C.F.R. § 1.821(c) and the computer readable file required by 37 C.F.R. § 1.821(c). The information contained in the Sequence Listing is incorporated by reference herein in its entirety.

Technical Field

The present disclosure relates to the field of biotechnology, in particular to an enhancing agent and a kit for enhancing nucleic acid amplification reaction and a method for performing nucleic acid amplification reaction.

Background Art

Polymerase Chain Reaction, called as PCR for short, is a widely used molecular biology technique. This technique allows exponential amplification of a particular nucleic acid fragment. In order to monitor the PCR reaction in real time, high resolution melting analysis (HRM) is used for identifying a PCR product, or a fluorescent indicator may be added to a PCR reaction solution. Fluorescent indicators for the PCR reaction are largely divided into two categories: one is fluorescent probe, such as Taqman probe, and molecular beacon probe; the other is fluorescent dye capable of binding to double-stranded DNA, such as EtBr, SYBR Green I (SGI), EvaGreen, and Sytox Green. Although the fluorescent probe can specifically bind to PCR products and used in a multiplex PCR reaction, synthesis of fluorescent probes is usually expensive. In addition, when the fluorescent probe is applied to different target nucleic acid sequences, complicated design and optimization of reaction conditions are required.

On the other hand, nucleic acid dye is inexpensive, and non-specific binding to double-stranded DNA allows their unlimited application to any double-stranded nucleic acid sequence. When the nucleic acid dye binds with double-stranded DNA, fluorescence intensity thereof can be enhanced to 1000 times, with extremely high sensitivity. However, such nucleic acid dye will inhibit amplification reactions at higher concentrations, such that their use is limited to low concentration ranges. Therefore, the inhibition of high-concentration nucleic acid dye to amplification reactions limits their use in PCR and relevant techniques.

Another drawback of double-stranded DNA fluorescent dye is their incompatibility with microfluidic systems. In recent years, PCR on a microfluidic chip (on-chip PCR) has become a research focus due to many advantages of the microfluidic systems such as low reagent consumption, fast reaction, and miniaturized size of devices. However, we have observed that in some microfluidic systems, the nucleic acid dye such as SGI produces false negative PCR results. Even though the amplification products have been identified by agarose electrophoresis, verifying successful amplification, SGI did not give a positive amplification signal. This phenomenon may be caused by diffusion of dye molecules into surrounding oil environment, or may be caused by adsorption of dye molecules by a chip surface. Kong and other researchers (Kong, J. E., Wei, Q., Tseng, D., Zhang, J., Pan, E., Lewiski, M., Garner, O. B., Ozcan, A. and Di Carlo, D. (2017) Highly Stable and Sensitive Nucleic Acid Amplification and Cell-Phone-Based readout. ACS nano, 11, 2934-2943.) also encountered the problem of reduced reliability and sensitivity of fluorescent dye on microfluidic chips for loop-mediated isothermal amplification (LAMP) that they developed. To this end, their solution is to add hydroxynaphthol blue (HNB) to reaction solutions, while the effect of HNB depends on ion concentration, and its function of enhancing PCR only can be adjusted by changing the HNB concentration to a limited extent.

In view of this, the present disclosure is specifically proposed.

SUMMARY

An object of the present disclosure is to provide an enhancing agent and a kit for enhancing nucleic acid amplification reaction and a method for performing nucleic acid amplification reaction. The enhancing agent for enhancing nucleic acid amplification reaction provided in the present disclosure not only can reduce inhibition of high-concentration fluorescent dye to amplification reaction, but also can enhance signal intensity of fluorescent dye in the nucleic acid amplification reaction based on microfluidic chip, improving reliability of application of the fluorescent dye as indicator of the nucleic acid amplification reaction on the microfluidic chip, and avoiding false negative results.

The present disclosure is realized as follows:

In a first aspect, an embodiment of the present disclosure provides an enhancing agent for enhancing nucleic acid amplification reaction, which is applicable to nucleic acid amplification reaction containing fluorescent dye, the fluorescent dye is capable of binding to double-stranded amplification products of the nucleic acid amplification reaction;
    the enhancing agent has a domain binding to the fluorescent dye and a quenching group for quenching fluorescence emitted by the fluorescent dye to which the domain binds, and the binding affinity of the domain to the fluorescent dye is lower than the binding affinity of a target amplification product of the nucleic acid amplification reaction to the fluorescent dye.

For the enhancing agent for enhancing nucleic acid amplification reaction provided in the embodiment of the present disclosure, its binding affinity to the fluorescent dye is lower than the binding affinity of the target amplification product to the fluorescent dye. When it is applied to nucleic acid amplification reaction, if there are fluorescent dye molecules of a higher concentration in a nucleic acid amplification reaction system, the domain of the enhancing agent is capable of binding to a part of the fluorescent dye molecules in the reaction system and can quench fluorescence emitted by these bound fluorescent dye molecules. The enhancing agent can temporarily store the fluorescent dye molecules, preventing a large amount of fluorescent dye molecules from being free in the solution to interfere with the amplification process.

As the amplification proceeds, amplification products having higher affinity to the fluorescent dye are produced, and as the amplification products have a higher affinity to the fluorescent dye, the fluorescent dye molecules temporarily stored in the enhancing agent actively transfer to the amplification products and release high-intensity fluorescence. Through such a mechanism of temporary storage and on-demand release, the enhancing agent provided in the embodiment of the present disclosure can effectively reduce the inhibition of high-concentration nucleic acid dye to amplification, without affecting the fluorescent dye's function as indicator of nucleic acid amplification reaction, and further enhance the performance of the nucleic acid amplification reaction.

Regarding the nucleic acid amplification reaction based on microfluidic chip, the enhancing agent provided in the embodiment of the present disclosure can effectively store the fluorescent dye molecules in the nucleic acid amplification reaction system, protect these fluorescent dye molecules, prevent them against damage before binding to the amplification products to affect the function as indicator, and further enhance the signal of the nucleic acid amplification reaction.

The enhancing agent provided in the embodiment of the present disclosure is applicable to any method requiring nucleic acid amplification reaction. The enhancing agent provided in the embodiment of the present disclosure can be added to the nucleic acid amplification reaction system to enhance the effect of the nucleic acid amplification reaction, as long as the nucleic acid amplification reaction involves use of the fluorescent dye binding to nucleic acid as indicator, for example, fluorescent nucleic acid amplification reaction, nucleic acid amplification reaction based on microfluidic control, as well as high resolution melting analysis.

In an optional embodiment, the enhancing agent is a DNA nucleic acid molecule, the DNA nucleic acid molecule has a double-stranded structure region bound by the base complementary pairing principle, and the domain capable of binding to the fluorescent dye is the double-stranded structure region; the quenching group is located at 5' end or 3' end of the double-stranded structure region.

It should be noted that the specific structure of the enhancing agent is not limited in the present disclosure, for example, it may have a DNA double-stranded structure, and also may have other structures that are capable of binding to the fluorescent dye. As long as an enhancing agent has a structure capable of binding to the fluorescent dye and its binding affinity to the fluorescent dye is lower than the affinity between the PCR amplification products and the fluorescent dye, it falls within the scope of protection of the present disclosure.

In an optional embodiment, the DNA nucleic acid molecule is a single-stranded DNA nucleic acid molecule, and the single-stranded DNA nucleic acid molecule has at least one stem structure region; the stem structure region is composed of a 5'-end stem region and a 3'-end stem region binding to each other through base complementary pairing; the double-stranded structure region is the stem structure region; the quenching group is located at the 5' end of the 5'-end stem region or the 3' end of the 3'-end stem region.

It should be noted that the number of strands of the DNA nucleic acid molecule is not limited in the present disclosure, for example, it may be a single-stranded DNA nucleic acid molecule, i.e. only having one 5' end and one 3' end, as long as it can form the double-stranded structure region capable of binding to the fluorescent dye by the base complementary pairing principle; in some other embodiments, the DNA nucleic acid molecule also may be double-stranded DNA nucleic acid molecule, i.e. a molecule formed by binding of two single-stranded nucleic acid molecules through base complementary pairing, which has two 5' ends and two 3' ends.

The double-stranded structure formed by one single-stranded DNA nucleic acid molecule is formed by a manner of intramolecular pairing, so that after the double-stranded structure dissociates by high-temperature denaturation in PCR, and when the temperature is reduced, intramolecular corresponding sequences of the single-stranded DNA nucleic acid molecule can be quickly and accurately re-paired into a double-stranded structure region. Whereas, the efficiency of the re-pairing after dissociation is low in the case of ordinary double-stranded DNA. In addition, the addition of double-stranded DNA nucleic acid molecules to the amplification reaction is likely to interfere with the amplification process, resulting in non-specific amplification. The "self-closing property" of the double-stranded structure region formed by self-complementation of the single-stranded DNA nucleic acid molecule allows it to not only have the double-stranded structure region, but also not easily interfere with the amplification reaction.

In an optional embodiment, a length of the stem structure region is shorter than a length of the amplification product. The length of the amplification product is not limited in the present disclosure, and generally, it is sufficient if the length of the amplification product is longer than the length of the stem structure region. Preferably, the amplification product is 50-1000 bp in length. The fluorescent dye is easier to bind to the DNA fragment of long fragment, the length of the stem structure region is controlled to be shorter than that of the amplification product, and the fluorescent dye bound to the stem structure region is easier to migrate to the amplification product along with the amplification, facilitating release of the fluorescent dye, and improving the fluorescence intensity.

In one or more embodiments, ratio of the length of the stem structure region to the length of a target amplification product is 1-16:100.

In one or more embodiments, a ratio of the length of the stem structure region to the length of a target amplification product is 2-16:100.

The ratio of the length of the stem structure region to the length of the target amplification product within a suitable range, for example, 2-16:100, can obviously improve the amplification effect of the nucleic acid amplification reaction, effectively reduce the inhibitory effect of high-concentration fluorescent dye, and improve the signal intensity of the fluorescent dye in the nucleic acid amplification reaction based on microfluidic chip. Preferably, the ratio of the length of the stem structure region to the length of the target amplification product is 2-9:100 or 10-16:100. More preferably, the ratio of the length of the stem structure region to the length of the target amplification product is 8.5:100.

The length of the stem structure region is one factor affecting the amplification effect. In an optional embodiment, the stem structure region has a length of 2-15 bp, and the stem structure region within this length range can achieve the objects of reducing the inhibitory effect of high-concentration fluorescent dye, and improving the signal intensity of the fluorescent dye in the nucleic acid amplification reaction based on microfluidic chip.

Preferably, the stem structure region has a length of 2-8 bp or 10-15 bp; more preferably, the stem structure region has a length of 8 bp. When the stem structure region has a length of 2-8 bp, preferably 8 bp, the enhancing agent provided in the embodiment of the present disclosure can, in an environment of high-concentration fluorescent dye, obviously improve the nucleic acid amplification reaction effect, overcome the inhibitory effect brought about by the high-concentration fluorescent dye, can realize successful amplification of a target sequence, and also can obviously improve the fluorescent signal intensity of the nucleic acid amplification reaction based on microfluidic chip.

In an optional embodiment, a base sequence of the 5'-end stem region of the stem structure region, from 5' end to 3' end, is CC, CCGC, CCGCTG, CCGCTGCG, CCGCTGCGCG (SEQ ID NO. 20) or CGTGCCGCTGGTCGC (SEQ ID NO. 21).

In an optional embodiment, the single-stranded DNA nucleic acid molecule further has a loop structure region.

The length of the loop structure region is not limited in the present disclosure. In an optional embodiment, the loop structure region has a length of 10-14 nt.

The base sequence of the loop structure region is not limited in the present disclosure. In an optional embodiment, a base of the loop structure region at any position is any one selected from A, T, C and G.

In an optional embodiment, a base of the loop structure region at any position is A.

In an optional embodiment, a linearized base sequence of the single-stranded DNA nucleic acid molecule is represented by any one of SEQ ID NOs. 1-7.

The single-stranded DNA nucleic acid molecule represented by any one of SEQ ID NOs. 1-7 can reduce and overcome the inhibitory effect brought about by high-concentration fluorescent dye, can realize successful amplification of target sequences, and can also remarkably improve the fluorescence signal intensity of nucleic acid amplification reaction based on microfluidic chip.

It should be noted that a person skilled in the art could select a suitable fluorescent dye to bind the amplification products according to actual need of the nucleic acid amplification reaction, for example, including but not limited to SYBR Green I, EvaGreen, Sytox Green, EtBr, SYBR Green II, SYBR Gold, SYBR Safe, LC Green, GelGreen, GelRed, DAPI, Syto 9, Sytox Blue, Sytox Red, Sytox Orange and Thiazole Orange. Whatever fluorescent dye is chosen, the fluorescent dye falls into the scope of protection of the present disclosure.

Of course, a person skilled in the art could select a suitable group that can absorb, for example by FRET mechanism, fluorescence emitted by the fluorescent dye according to the type of fluorescent dye, for example, including but not limited to, any one of BHQ, BHQ 1, BHQ 2, BHQ 3, Dabcyl and TAMRA. Whatever quenching group is chosen, the quenching group falls into the scope of protection of the present disclosure.

In an optional embodiment, the above nucleic acid amplification reaction is any one selected from polymerase chain reaction (PCR) and isothermal amplification reaction.

The enhancing agent provided in the present disclosure can be applied to all nucleic acid amplification reactions in which the amplification product is double-stranded DNA, and these amplification reactions are not limited to the above-mentioned PCR and LAMP, and also may be other nucleic acid amplification reactions, and any nucleic acid amplification reaction used is within the scope of protection of the present disclosure.

In a second aspect, an embodiment of the present disclosure provides a nucleic acid amplification reaction solution, containing the enhancing agent according to any one of the above embodiments.

In a third aspect, an embodiment of the present disclosure provides a digital microfluidic chip for performing nucleic acid amplification reaction, loaded with the above nucleic acid amplification reaction solution or having a structure loading the above nucleic acid amplification reaction solution.

It should be noted that the enhancing agent provided in the present disclosure can be applied to all microfluidic platforms performing nucleic acid amplification that is based on nucleic acid dyes. Whatever microfluidic platforms is chosen, it falls into the scope of protection of the present disclosure.

In a fourth aspect, an embodiment of the present disclosure provides a kit for nucleic acid amplification reaction, containing the enhancing agent for enhancing nucleic acid amplification reaction according to the any one of above embodiments or the nucleic acid amplification reaction solution as described in the above.

In a fifth aspect, an embodiment of the present disclosure provides a method for performing nucleic acid amplification reaction, which includes: adding, to a nucleic acid amplification reaction system, the enhancing agent for enhancing nucleic acid amplification reaction according to any one of the above embodiments or the nucleic acid amplification reaction solution as described in the above.

In an optional embodiment, the enhancing agent in the nucleic acid amplification reaction system has a concentration of 50-2000 nM, preferably, 100-900 nM.

In an optional embodiment, the nucleic acid amplification reaction system contains a fluorescent dye, and the fluorescent dye is any one selected from the group consisting of SYBR Green I, EvaGreen, Sytox Green, EtBr, SYBR Green II, SYBR Gold, SYBR Safe, LC Green, GelGreen, GelRed, DAPI, Syto 9, Sytox Blue, Sytox Red, Sytox Orange and Thiazole Orange.

It should be noted that a person skilled in the art could select a suitable fluorescent dye to bind the amplification products according to actual need of the nucleic acid amplification reaction, for example, including but not limited to SYBR Green I, EvaGreen, Sytox Green, EtBr, SYBR Green II, SYBR Gold, SYBR Safe, LC Green, GelGreen, GelRed, DAPI, Syto 9, Sytox Blue, Sytox Red, Sytox Orange and Thiazole Orange. Whatever fluorescent dye is chosen, the fluorescent dye falls into the scope of protection of the present disclosure.

Of course, a person skilled in the art could select a suitable quenching group that can absorb fluorescence emitted by the fluorescent dye according to the type of fluorescent dye, for example, including but not limited to, any one of BHQ, BHQ 1, BHQ 2, BHQ 3, Dabcyl and TAMRA. Whatever quenching group is chosen, the quenching group falls into the scope of protection of the present disclosure.

In an optional embodiment, the fluorescent dye is SYBR Green I, and the concentration of the fluorescent dye is 0.2×-2× in the nucleic acid amplification reaction system.

In an optional embodiment, the nucleic acid amplification reaction is any one selected from polymerase chain reaction and isothermal amplification reaction.

In an optional embodiment, the polymerase chain reaction is real-time fluorescent polymerase chain reaction, polymerase chain reaction based on microfluidic chip, or high resolution melting analysis. In an optional embodiment, the method is real-time fluorescent nucleic acid amplification reaction, nucleic acid amplification reaction based on microfluidic chip or high resolution melting analysis.

BRIEF DESCRIPTION OF DRAWINGS

In order to more clearly illustrate technical solutions of examples of the present disclosure, accompanying drawings which need to be used in the examples will be introduced briefly below. It should be understood that the accompanying drawings below merely show some examples of the present disclosure, therefore, they should not be considered as limitation to the scope, and a person ordinarily skilled in the art still could obtain other relevant accompanying drawings according to these accompanying drawings, without using inventive efforts.

FIG. 2A-FIG. 2F show enhancement effect of an enhancing agent on off-chip PCR and on-chip PCR. The enhancing agent used in this experiment is 500 nM A4Q. (FIG. 2A) Comparison of amplification curves of enhancing agent-free samples and of enhancing agent-containing samples when SGI concentrations are 0.4×, 0.8×, 1.2×, and 1.6×, respectively, in off-chip PCR.

(FIG. 2B, C) Top view and side view of a digital microfluidic chip used in the present experiment. (FIG. 2D) Comparison of fluorescence intensities of enhancing agent-free samples and of enhancing agent-containing samples when SGI concentrations are 0.4×, 0.8×, 1.2×, and 1.6×, respectively, in on-chip PCR. (FIG. 2E) Comparison of fluorescence micrographs of enhancing agent-free samples and of enhancing agent-containing samples before and after on-chip PCR when SGI concentration is 0.4×. (FIG. 2F) Agarose gel electrophoresis analysis diagram of on-chip PCR products in FIG. 2E, wherein three parallel samples under corresponding conditions are fused in each column, and M represents DNA markers.

(FIG. 3A) Enhancement effect of the enhancing agent on off-chip PCR when the stem length is from 0 bp to 20 bp (A0Q~A20Q). (FIG. 3B) Enhancement effect of the enhancing agent on on-chip PCR when the stem length is from 0 bp to 20 bp (A0Q~A20Q). (FIG. 3C) Enhancement effect of A8Q of different concentrations (100 nM~900 nM) on off-chip PCR. (FIG. 3D) Enhancement effect of A8Q of different concentrations (100 nM~900 nM) on on-chip PCR.

(FIG. 4A) Structural schematic diagram of A4Q. (FIG. 4B) Structural schematic diagram of A4 spacer, wherein an original quenching group at 3' end is replaced by C3 spacer. (FIG. 4C) Structural schematic diagram of F-CRoA, wherein in a loop structure, an original AAAAAAAAAAAAA sequence (poly A sequence, as shown in SEQ ID NO. 22) is replaced by a sequence which is specifically complementary with a target nucleic acid. (FIG. 4D) Enhancement effect of A4 spacer, A4Q and F-CRoA on off-chip PCR in the cases of 0.4×SGI and 0.8×SGI. (FIG. 4E) Enhancement effect of A4 spacer, A4Q and F-CRoA on on-chip PCR in the case of 0.4×SGI.

(FIG. 6A) Comparison of amplification curves of enhancing agent-free samples and of enhancing agent-containing samples when Sytox Green has a concentration of 200 nM 500 nM in off-chip PCR. (FIG. 6B) Comparison of amplification results of enhancing agent-free samples and of enhancing agent-containing samples when Sytox Green has a concentration of 200 nM in on-chip PCR. (FIG. 6C) Comparison of amplification curves of enhancing agent-free samples and of enhancing agent-containing samples when EvaGreen concentrations are 1×, 3×, 4×, and 5×, respectively, in off-chip PCR. (FIG. 6D) Comparison of amplification results of enhancing agent-free samples and of enhancing agent-containing samples when EvaGreen has a concentration of 1× in on-chip PCR.

DETAILED DESCRIPTION OF EMBODIMENTS

Figure 1:
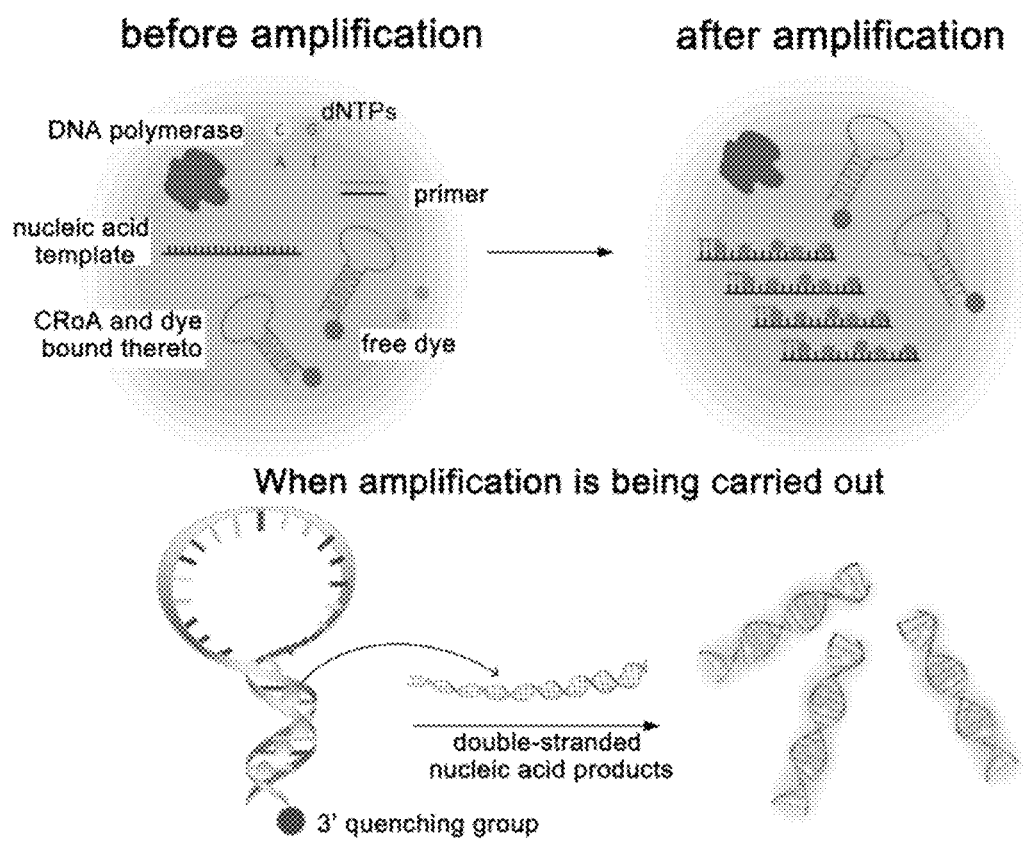
FIG. 1 is a schematic diagram showing the mechanism of enhancing nucleic acid amplification reaction by an enhancing agent (CRoA, CRoA in FIG. 1-FIG. 7 represents the enhancing agent of the present disclosure) provided in Example 1 of the present disclosure.

In order to make objects, technical solutions and advantages of the examples of the present disclosure more clear, the technical solutions in the examples of the present disclosure will be described clearly and completely below. If no specific conditions are specified in the examples, they are carried out under normal conditions or conditions recommended by the manufacturer. If the manufacturers of reagents or apparatus used are not specified, they are conventional products commercially available.

Features and performances of the present disclosure are further described below in detail in combination with examples.

Example 1

An enhancing agent for enhancing nucleic acid amplification reaction provided in the present example was a single-stranded DNA nucleic acid molecule, wherein the single-stranded DNA nucleic acid molecule as a whole was in a hairpin structure, a partial sequence of a 5' end thereof acted as a 5'-end stem region, a partial sequence of 3' end acted as a 3'-end stem region, the 5'-end stem region binds with the 3'-end stem region through base complementary pairing, forming a stem structure region capable of binding with fluorescent dye, the stem structure region had a length of 2 bp, a base sequence of the 5'-end stem region from the 5' end to the 3' end was CC, a 10 nt-long loop structure region was between the 5'-end stem region and the 3'-end stem region, and a base at any position of the loop structure region was A; in addition, the 3' end of the 3'-end stem region had a fluorescence quenching group BHQ.

A linearized base sequence of the single-stranded DNA nucleic acid molecule provided in the present example is as represented by SEQ ID NO. 1. See Table 1 for a specific sequence.

Examples 2-7

Enhancing agents for enhancing nucleic acid amplification reaction provided in Examples 2-6 were substantially the same as that in Example 1, except that lengths and sequences of stem structure regions were different, and lengths of loop structure regions were different. See Table 1 for specific sequences of Examples 2-7 (SEQ ID NOs. 2-7).

Comparative Example 1

An enhancing agent for enhancing nucleic acid amplification reaction provided in Comparative Example 1 was substantially the same as that in Example 1, except that length and sequence of stem structure region were different, and length of loop structure region was different. See Table 1 for a specific sequence (SEQ ID NO. 8).

Comparative Example 2

An enhancing agent for enhancing nucleic acid amplification reaction provided in Comparative Example 2 was substantially the same as that in Example 2, except that a quenching group thereof was replaced by C3 spacer. See Table 1 for a specific sequence (SEQ ID NO. 9).

Comparative Example 3

An enhancing agent for enhancing nucleic acid amplification reaction provided in Comparative Examples 3 was substantially the same as that in Example 1, except that there was no stem structure region. See Table 1 for a specific sequence (SEQ ID NO. 10).

TABLE 1

Nucleic Acid Sequences Involved in Examples, Comparative Examples and Experimental Examples of the Present Disclosure

| Examples | Name | Total Length/nt | Double-Strand Length in Stem Structure Region/bp | Length in Loop Structure Region/nt | Sequence | SEQ ID NO. |
|---|---|---|---|---|---|---|
| 1 | A2Q | 14 | 2 | 10 | 5'-CCAAAAAAAAAAGG-BHQ2-3' | 1 |
| 2 | A4Q | 22 | 4 | 14 | 5'-CCGCAAAAAAAAAAAAAAGCGG-BHQ2-3' | 2 |
| 3 | A6Q | 26 | 6 | 14 | 5'-CCGCTGAAAAAAAAAAAAAACAGCGG-BHQ2-3' | 3 |
| 4 | A8Q | 30 | 8 | 14 | 5'-CCGCTGCGAAAAAAAAAAAAAAACGCAGCGG-BHQ2-3' | 4 |
| 5 | A10Q | 34 | 10 | 14 | 5'-CCGCTGCGCGAAAAAAAAAAAAAACGCGCAGCGG-BHQ2-3' | 5 |
| 6 | A15Q | 44 | 15 | 14 | 5'-CGTGCCGCTGGTCGCAAAAAAAAAAAAAAGCGACCAGCGGCACG-BHQ2-3' | 6 |
| 7 | F-CRoA | 23 | 4 | 14 | 5'-CY5-CCGGACTCTGCTTGTTATGCCGG-BHQ2-3' | 7 |

TABLE 1-continued

Nucleic Acid Sequences Involved in Examples, Comparative Examples and Experimental Examples of the Present Disclosure

| Examples | Name | Total Length/nt | Double-Strand Length in Stem Structure Region/bp | Length in Loop Structure Region/nt | Sequence | SEQ ID NO. |
|---|---|---|---|---|---|---|
| Comparative Example 1 | A20Q | 54 | 20 | 14 | 5'-<u>CGTGCCGCTG GTTCGCTGGC</u>AAAAAAAAAA AAAAGCCAGC<u>GAACCAGCGG CACG</u>-BHQ2-3' | 8 |
| Comparative Example 2 | A4spa | 22 | 4 | 14 | 5'CCGCAAAAA AAAAAAAAG CGG-C3 spacer | 9 |
| Comparative Example 3 | A0Q | 10 | none | 10 | 5'-AAAAAAAAAA-BHQ2-3' | 10 |

In the table, underlines represent stem region sequences.

In the above, specific names of each enhancing agent for enhancing the nucleic acid amplification reaction provided in Examples 1 to 7 are shown in Table 1. See FIG. 1 for the mechanism by which the enhancing agents provided in Examples 1-7 of the present disclosure function to reduce inhibitory effect of high-concentration fluorescent dye. As shown in FIG. 1, these enhancing agents are a segment of nucleic acid sequences with a hairpin structure, with a quenching group at a 3' end thereof. A stem structure region of the hairpin structure, which is a segment of double-stranded DNA, is capable of binding to nucleic acid fluorescent dye, and serve as a temporary storage pool for the fluorescent nucleic acid dye, and the presence of the quenching group enables the fluorescent dye not to emit fluorescence. As the amplification reaction proceeds, the fluorescent dye will jump to longer amplification products of a double-stranded DNA, and emit high-intensity fluorescence. Through a series of experiments, we proved the enhancement efficacy of the enhancing agents of Examples 1-7 for nucleic acid amplification reaction, and the enhancing agents not only can reduce inhibition of high-concentration nucleic acid dye to amplification reaction, but also can enhance nucleic acid amplification reaction on a microfluidic chip.

Experimental Example 1

(1) Materials:

A nucleic acid template was a sequence with length of 311 bp containing the G269 allelic site of human aminohexaglycosidase A gene, as follows:

SEQ ID NO. 11
5'-CGAGGTCATTGAATACGCACGGCTCCGGGGTATCCGTGTGCTTGCA

GAGTTTGACACTCCTGGCCACACTTTGTCCTGGGGACCAGGTA<u>AGA</u>

<u>ATGATGTCTGGGACCAGAGGG</u>ACTCTGCTTGTTATGCTCAGAGTGA

AGCTTCAGGGCACTGGCTCATGGAAGTGGCATATCCCAGCTTGGTC

CTTAGAAGAATGTTTTCCATCGACTTCTTCCACCTGGGAATTTAGA

TAGGAAGAACTCACTTTGGACAATGGAGGCTGCTTCTTACTATTAA

AATATGTACTGTTAGACTATGTAAGGGCACAGCGC-3'.

The underline represents a target amplification region. A PCR target amplification product was a double-stranded DNA having a length of 94 bp.

Primers used to amplify the sequence of the gene were as follows:

Upstream primer sequence:
(SEQ ID NO. 12)
5'GAATGATGTCTGGGACCAGA3';

Downstream primer sequence:
(SEQ ID NO. 13)
5'GACCAAGCTGGGATATGCC3'.

All nucleic acid fragments were synthesized by Sangon Biotech (Shanghai).

Length ratios of various enhancing agents in Table 1 to target products are shown in Table 2:

| Name | Length of Stem Structure Region/bp | Length of Target Amplification Product/bp | Length Ratio |
|---|---|---|---|
| A2Q | 2 | 94 | 2.1:100 |
| A4Q | 4 | 94 | 4.3:100 |
| A6Q | 6 | 94 | 6.4:100 |
| A8Q | 8 | 94 | 8.5:100 |
| A10Q | 10 | 94 | 10.6:100 |
| A15Q | 15 | 94 | 16:100 |
| A20Q | 20 | 94 | 16:100 |

(2) Method:
(a) Real-Time Fluorescent PCR (Off-Chip PCR)

A real-time fluorescent nucleic acid amplification reaction solution in the present experiment had a volume of 10 μL, containing 1×PCR buffer (Invitrogen, USA), 3 mM $MgCl_2$ (Invitrogen, USA), 200 nM dNTP (Invitrogen, USA), 200 nM upstream primer and 200 nM downstream primer, 0.04 μL Platinum™ Taq DNA polymerase (Invitrogen, USA). For positive samples, $1\times10^6$ copies of template were added to the reaction solution, and ultrapure water, instead of the template, was added to the negative sample reaction solution. Depending on the experimental design, the reaction solution also contained SGI of different concentrations (purchased from Invitrogen as 10000× concentrate in DMSO, cat # S7563) or EvaGreen (purchased from Biotium as 2000× in DMSO, cat # 31019), Sytox Green. Unless particularly stated, the concentration of the enhancing agent was 500 nM. The off-chip reaction was performed on a Biorad CFX96 real-time fluorescent PCR instrument, with the following amplification procedure: hot start at 95° C. for 2 min, 50 cycles of 95° C. for 5 s and 58° C. for 15 s, and a following melting analysis procedure was: from 35° C. to 95° C., residing at each temperature for 2 s at an interval of 1° C. Three parallel samples were made for each off-chip nucleic acid amplification reaction.

(B) Nucleic Acid Amplification Reaction Based on Microfluidic Chip (On-Chip PCR)

1.1 μL of the reaction solution used for the real-time fluorescence PCR was added to a digital microfluidic chip for on-chip nucleic acid amplification reaction. The droplet on the chip was surrounded by 2 cSt silicone oil. Before reaction, the chip was placed under a fluorescence microscope to collect fluorescence of a GFP channel. Subsequently, the chip was placed on an AmpliSpeed planar thermocycler for temperature cycling required by the amplification. After the amplification was ended, when the chip was cooled to room temperature, the chip was again placed under the fluorescence microscope to collect fluorescence of the GFP channel. Three parallel samples were made simultaneously each time for the on-chip nucleic acid amplification reaction.

For several early experiments, the droplet was taken out from the chip after the amplification was ended, and subjected to agarose gel electrophoresis to identify amplification products. The agarose gel concentration was 3%, and molecular markers as controls were small-molecular-weight DNA markers of 25 bp to 766 bp.

Preparation and Operation of the Digital Microfluidic Chip

Figure 2A:
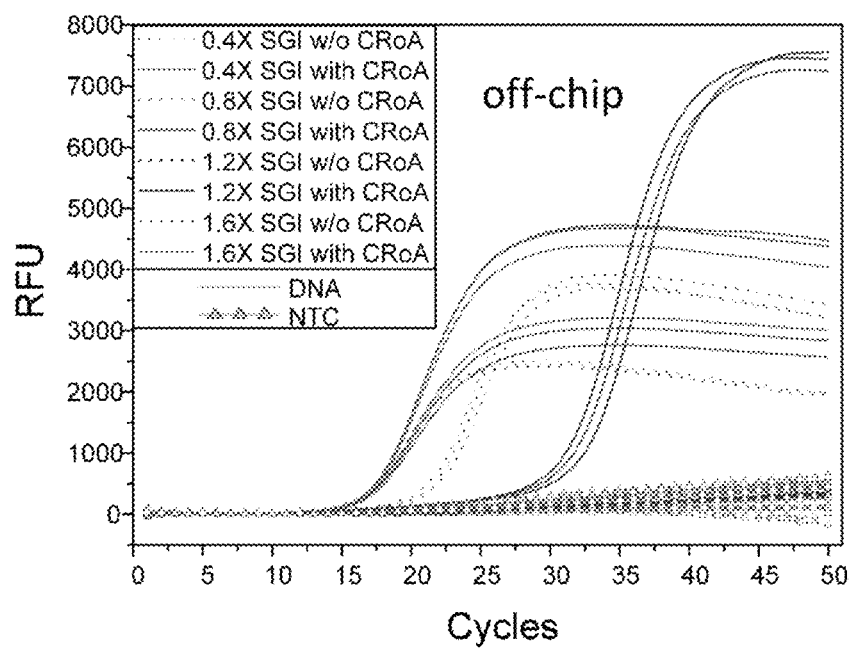
Figures 2B, 2C:
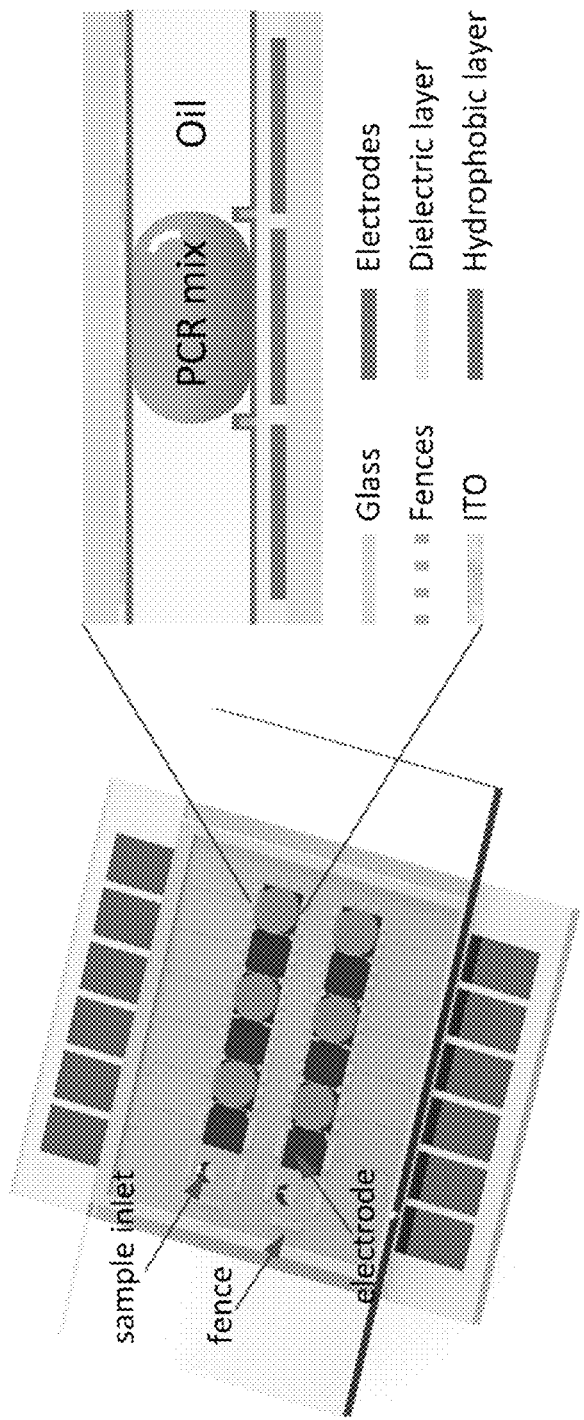

The digital microfluidic chip used in the present experiment is as shown in FIG. 2B and FIG. 2C. Chromium electrodes having a size of 2 mm×2 mm were arranged on a glass substrate, and a layer of SU-8 3010 having a thickness of about 10 μm was applied as a dielectric layer on the electrodes by photolithography. Another layer of SU-8 3050 having a thickness of 50-60 μm was also applied on the dielectric layer by photolithography, as a "fence" for preventing droplet drift. A top plate was also of glass, with one face being plated with ITO as a ground electrode. After a bottom plate and a top plate both have undergone Teflon hydrophobic treatment, both upper and lower portions were assembled together using a double-sided tape having a thickness of 300 μm, wherein a face of the top plate having the ITO faces downwards. When loading and moving the droplets, an electrical signal used to drive the electrodes was a sine wave of 90-100 Vrms and 1 kHz.

Data Processing and Result Identification for On-Chip PCR

For the on-chip nucleic acid amplification reaction, fluorescence data before and after amplification were collected at room temperature through a fluorescence microscope and supporting software. Fluorescence data for corresponding sample was obtained by subtracting background fluorescence of at least 3 surrounding spots from average fluorescence intensity of each droplet. The fluorescence intensities before and after amplification were recorded as "F pre" and "F post", respectively. As the fluorescence intensities before amplification "F pre" of different samples will be inconsistent due to multiple factors, in order to facilitate the comparison of on-chip PCR amplification results of different samples, we calculated the change in fluorescence intensity of each amplification reaction by (F post−F pre)/F pre× 100%, thereby normalizing the data.

(3) Results (a) The Enhancing Agents of Examples 1-7 Enhance PCR by Reducing Inhibition of High-Concentration Nucleic Acid Dye to Amplification Reaction As shown in FIG. 2A, high-concentration SGI inhibits PCR. Compared with commonly used 0.4×SGI, a Cq value has a delay of 3 cycles when the SGI concentration is increased to 0.8×. Continued increase in the SGI concentration to 1.2× directly results in amplification failure.

However, the enhancing agents provided in the examples of the present disclosure greatly reduced the inhibitory effect caused by such high-concentration nucleic acid dye. For samples in which the reaction solution contains the above enhancing agents, 0.8×SGI no longer inhibits the amplification reaction, and although 1.2×SGI still caused a delay of Cq value, the amplification is successful. The effect of the above enhancing agents in this respect is attributed to their structures. When nucleic acid dye molecules of a higher concentration are present in a solution, the double-stranded stem structures of the above enhancing agents can temporarily store the dye molecules, preventing a large amount of dye from being free in the solution to interfere with the amplification process. As the amplification proceeds, longer double-stranded DNA nucleic acid products are produced, and as the longer double-stranded DNA has higher affinity to the nucleic acid dye, the dye molecules temporarily stored on the above enhancing agents actively transfer to the amplification products and release high-intensity fluorescence. Through such a mechanism of temporary storage and on-demand release, the above enhancing agents can reduce the inhibition of high-concentration nucleic acid dye to amplification, without affecting the function of the nucleic acid dye as an amplification indicator.

Besides, the above enhancing agents further can increase the fluorescence intensity at the saturation stage. As shown in FIG. 2A, when the SGI concentration is 0.4×, presence of the above enhancing agents does not change the Cq value, but compared with the samples not containing the above enhancing agents, the samples containing the above enhancing agents have slightly higher fluorescence intensity in the amplification plateau. This is because the presence of the quenching group allows the dye molecules bound to the stem structure of the above enhancing agents to have a lower fluorescence intensity than free dye molecules (see FIG. 2E), and the samples containing the above enhancing agents have the fluorescence intensity, in the early stage of PCR, lower than the samples not containing the above enhancing agents, therefore, after baseline correction of the amplification curve, the samples containing the above enhancing agents have a higher saturation fluorescence value.

Results in FIG. 2A also show that SGI is allowed to be used at higher concentrations due to the presence of the above enhancing agents, and the fluorescence intensity is multiplied at the end of amplification, which gives SGI the potential of being applied to high-resolution melting (HRM) analysis (b) The Above Enhancing Agents of Examples 1-7 can Enhance the Fluorescence Intensity Change of On-Chip PCR and Eliminate False Negative Amplification Results on the Chip.

Figure 2D:
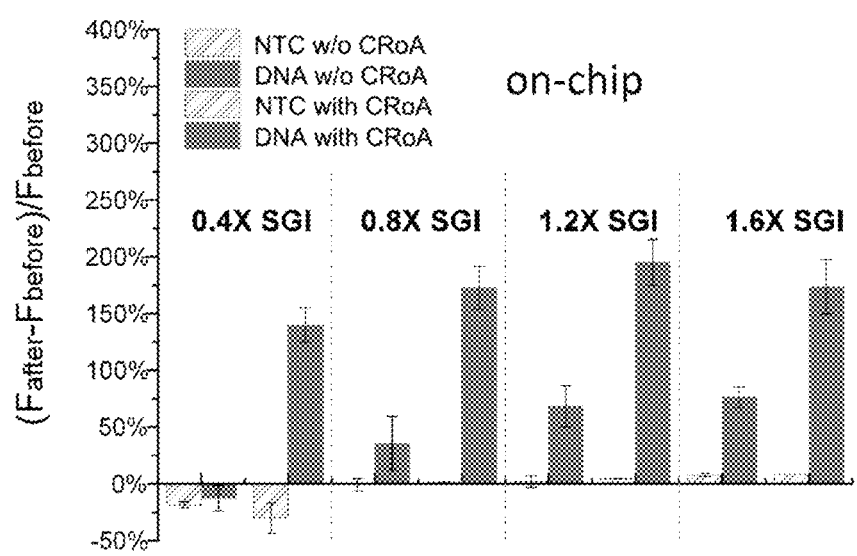

As shown in FIG. 2D, when SGI is applied to a digital microfluidic chip, its effect as an indicator is greatly impaired. When SGI is 0.4×, a common concentration, even if the amplification is successful (as shown in FIG. 2F), the fluorescence intensity of SGI does not increase, resulting in a false negative result on the chip. Although increasing the SGI concentration can enhance the fluorescence value after amplification to a certain extent, and eliminate false negative, the increase in fluorescence intensity thereof is still less than 100%. This phenomenon that the nucleic acid dye is impaired in fluorescence intensity on the chip may be caused by various factors such as penetration of dye molecules into surrounding oil environment or adsorption by a chip surface.

Regardless of the cause of SGI's failure on the digital microfluidic chip, the above enhancing agents can settle the incompatibility between the nucleic acid dye and the microfluidic chip, and reconstruct the application of SGI as PCR indicator on the chip. As shown in FIG. 2D, after the above enhancing agents are added to the samples, the fluorescence of the nucleic acid dye after amplification increases by 150% (0.4×SGI)~200% (0.8×~1.6×SGI) from reducing. FIG. 2E more intuitively shows that positive samples containing the above enhancing agents successfully illuminate after amplification on the chip. Identical to the mechanism of action in off-chip PCR, the enhancement effects of the above enhancing agents on on-chip PCR come from their special structures, as well as their mechanism of temporary storage and on-demand release. However, the difference is that when the inhibitory effect is reduced, the above enhancing agents adsorb free dye molecules for the purpose of preventing them from interfering with the PCR procedure, while in on-chip PCR, the above enhancing agents adsorb the dye molecules for the purpose of protecting them, and preventing them from being damaged to affect the function as indicator.

Besides, the above enhancing agents further can reduce the fluorescence intensity of the samples before amplification, and improve the fluorescence contrast before and after amplification. As shown in FIG. 2E, droplets containing the above enhancing agents, before PCR, are darker than droplets not containing the above enhancing agents, such that the fluorescence intensities before and after amplification change more significantly.

Figure 3A:
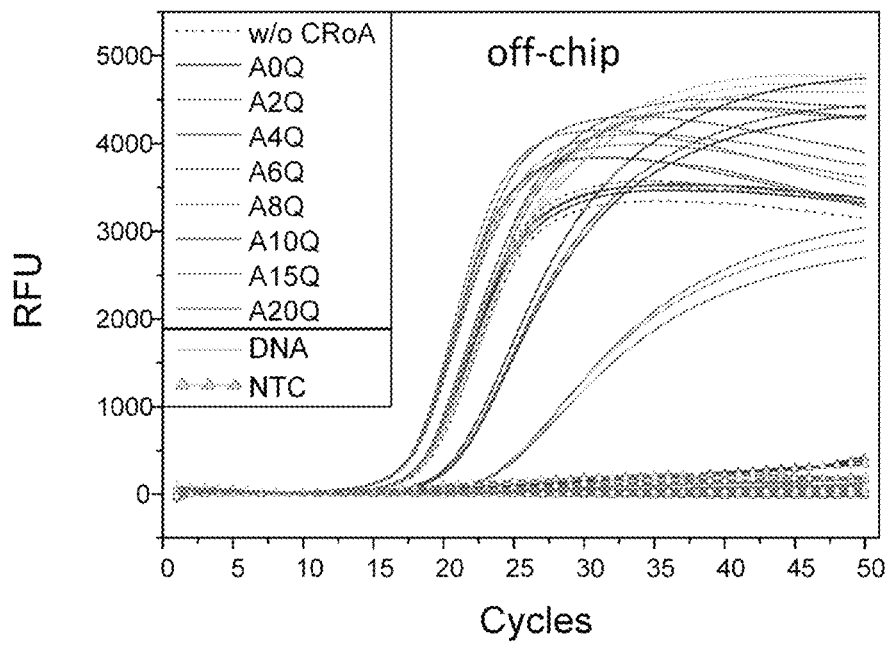
FIG. 3A-FIG. 3D show influences of stem length and concentration of the enhancing agent on off-chip PCR and on-chip PCR. SGI concentration is 0.4× in the experiment.
Figure 3B:
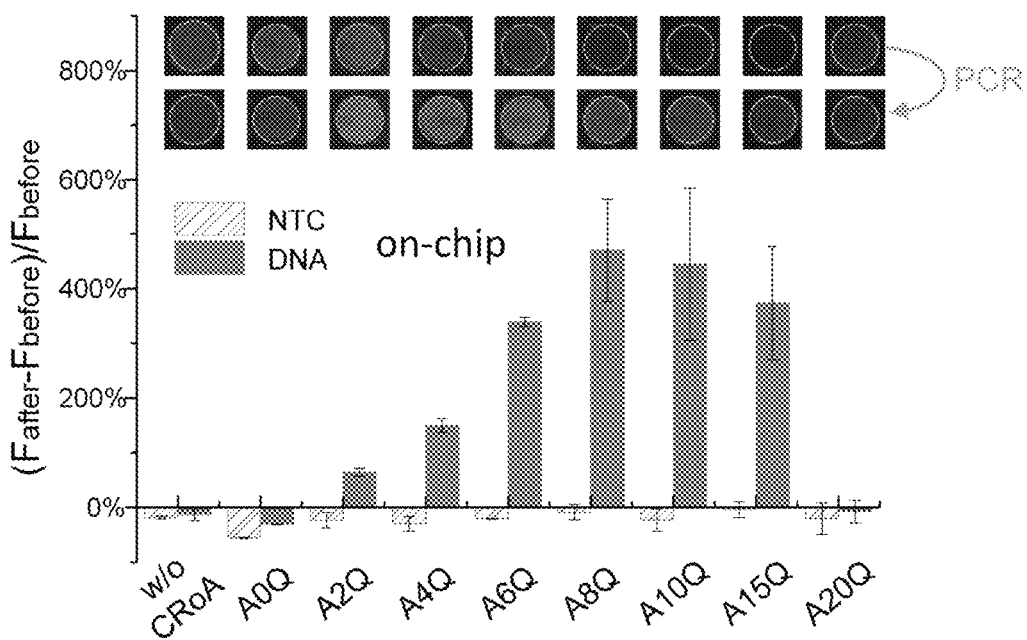

(c) Efficacies of the Stem Structure Length and Concentration of the Above Enhancing Agents for Enhancing PCR FIG. 3A and FIG. 3B demonstrate efficacies of the above enhancing agents of different stem lengths in off-chip PCR and on-chip PCR.

In off-chip PCR, there is no significant difference in amplification efficiency when the stem length is 2 bp~8 bp. When the stem length is greater than or equal to 10 bp, the above enhancing agents inhibit amplification: A10Q causes the Cq value to be delayed by 3 cycles, A15Q causes the Cq value to be delayed by more than 5 cycles, and A20Q provided in Comparative Example 1 directly causes failure of amplification. On the other hand, in on-chip PCR, the above enhancing agents having a stem length between 2 bp and 15 bp produce an effect of enhancing on-chip PCR amplification signal. In the above, A8Q has the strongest enhancement effect: for the application of the positive sample containing 500 nM A8Q on the chip, the fluorescence signal is enhanced by 500%. This result is relatively consistent with off-chip PCR: as the stem length of the above enhancing agents increase, the above enhancing agents can provide more binding sites to the free SGI molecules in the solution, and enhance the above enhancing agents' function of enhancing PCR, and the above enhancing agent performs best when the stem length is 8 bp. A20Q provided in Comparative Example 1 directly leads to the failure of on-chip PCR amplification. In addition, the A0Q provided in Comparative Example 3 cannot improve the PCR amplification signal on the chip, proving that the stem structure of the above enhancing agents is a key composite part for realizing the function of enhancing PCR. Therefore, this experiment fully demonstrates that the stem structure length of the above enhancing agents limited between 2 bp and 15 bp is preferable, wherein the length of 8 bp is more preferable.

Figure 3C:
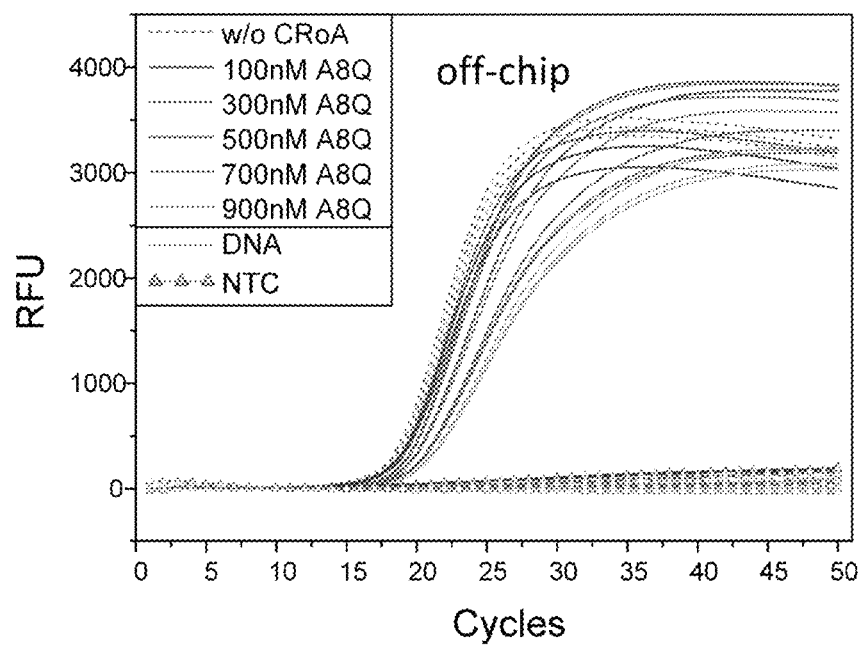
Figure 3D:
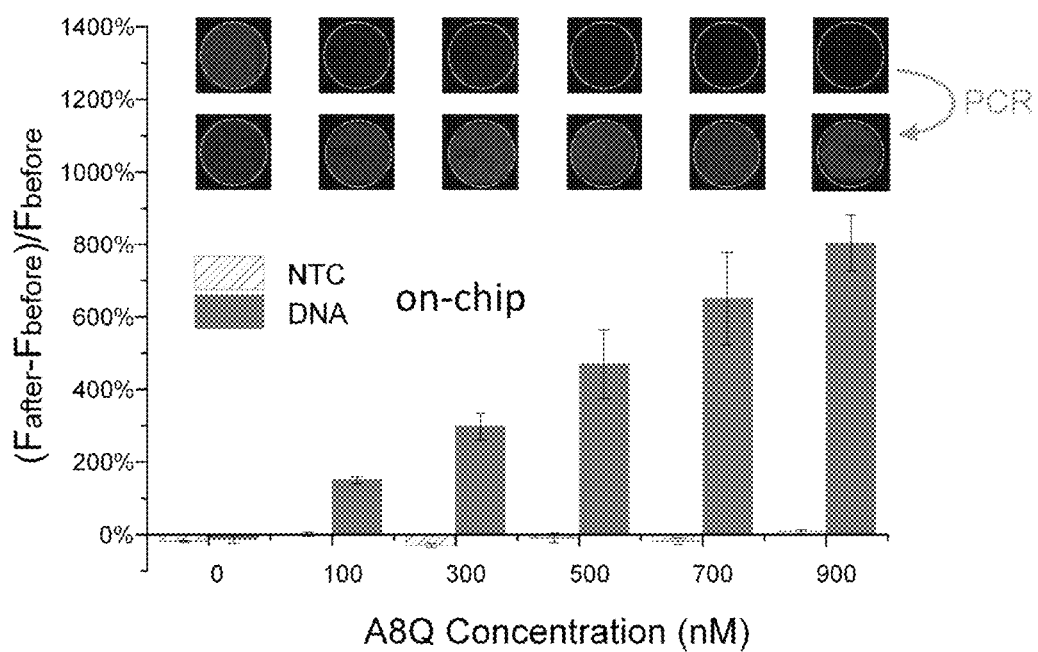

Subsequently, taking A8Q as a model, we tested the performance of different concentrations of A8Q in PCR. As shown in FIG. 3C, when the concentration of A8Q is increased from 100 nM to 900 nM, there is no significant difference in the performance of off-chip PCR, and the change in the Cq value is within 1~2 cycles. However, for on-chip PCR, the higher the concentration of the above enhancing agents is, the more significant the amplification signal is enhanced, and at 900 nM A8Q, the increase in SGI fluorescence signal after amplification reaches 800%. On the chip, the higher the concentration of the above enhancing agents in a certain range, the more binding sites can be provided to the free dye molecules, the stronger the protection can be provided for nucleic acid dye, and thus the more significant the enhancement to on-chip PCR is.

(d) Influences of Quenching Group and Loop Structure on the Above Enhancing Agents Structure of the above enhancing agents mainly consists of a hairpin structure composed of a stem and a loop, and a quenching group at 3' end. Results in FIG. 3B have proved the importance of the stem structure to the above enhancing agents' function of enhancing PCR. In order to test the function of the quenching group, we synthesized A4 spacer in Comparative Example 2. A nucleic acid sequence of A4 spacer is identical to that of A4Q, except that 3' end of A4 spacer is modified with a C3 spacer to replace the quenching group (see Table 1). C3 spacer functions to block the 3' end, preventing non-specific amplification. Furthermore, in order to test influence of the loop sequence on the above enhancing agents, we further synthesized a sequence structurally similar to the above enhancing agents, but having a fluorophore at 5' end thereof, and a loop sequence thereof was complementary to the target nucleic acid sequence.

Figure 4A:
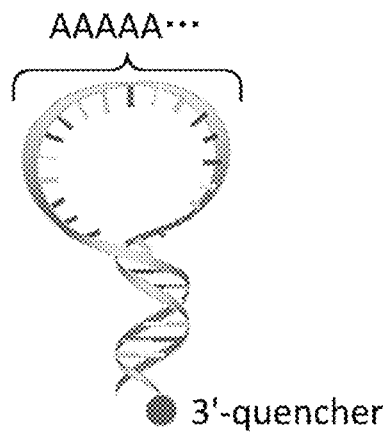
FIG. 4A-FIG. 4E show influences of quenching group and loop sequence of the enhancing agent on off-chip PCR and on-chip PCR.
Figure 4B:
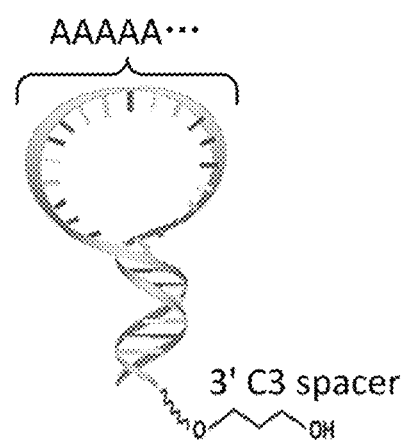
Figure 4C:
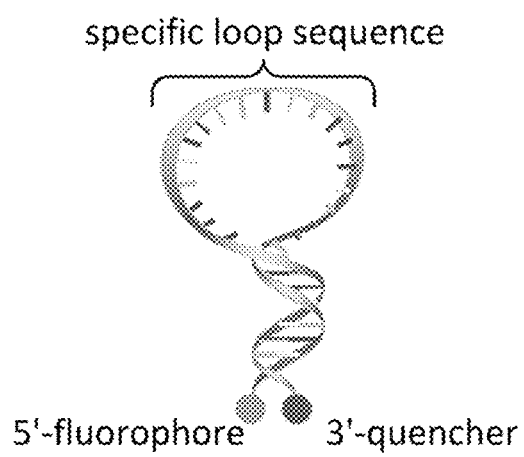
Figure 4D:
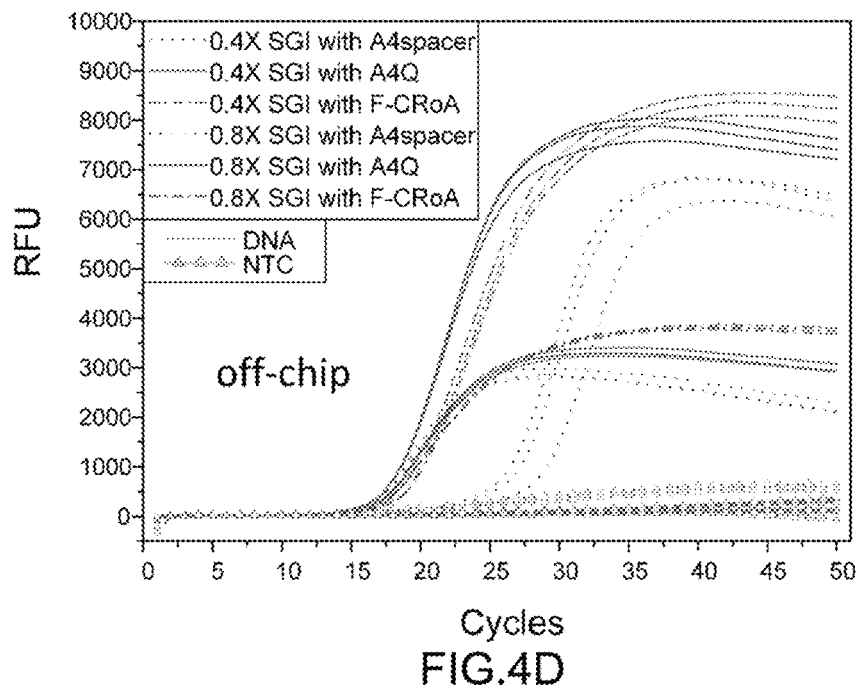
Figure 4E:
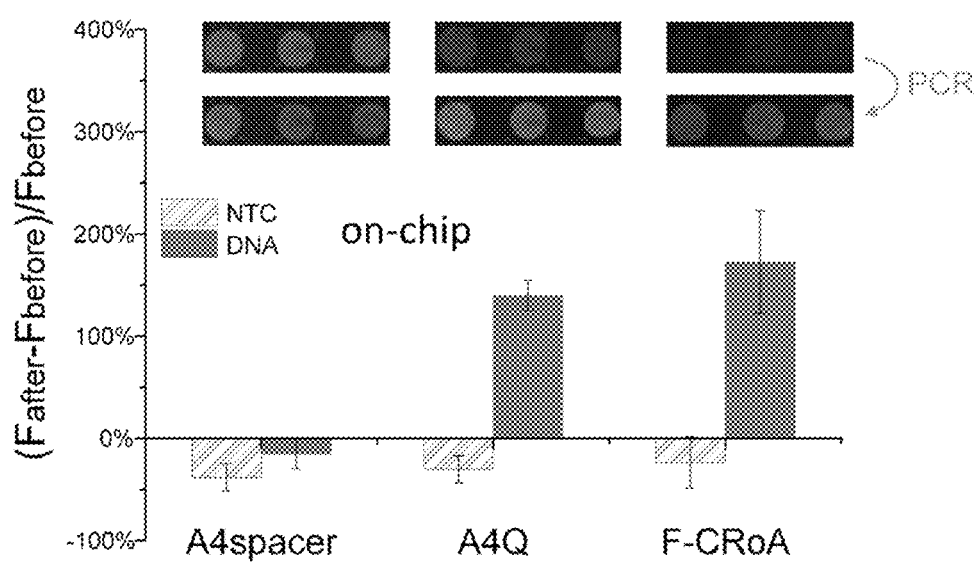

As shown in FIG. 4C and FIG. 4D, A4 spacer neither can enhance off-chip PCR nor can enhance the amplification signal of on-chip PCR. On the other hand, in both off-chip PCR and on-chip PCR, F-CRoA exhibits the effect of enhancing PCR consistent with A4Q. For off-chip PCR, at 0.8×SGI, the Cq value of the sample containing A4 spacer caused delay by 5 cycles compared with that at 0.4×SGI, while the sample containing A4Q or F-CRoA still does not inhibit amplification at a higher concentration of SGI. For on-chip PCR, after the amplification, the positive sample containing A4 spacer does not illuminate, while the positive sample containing A4Q or F-CRoA successfully illuminates, indicating that A4 spacer cannot enhance the amplification signal of on-chip PCR, while F-CRoA can enhance the amplification signal of on-chip PCR. Accordingly, the above experiments indicate that in the structures of the above enhancing agents, the quenching group is a key component, and specificity of the loop sequence does not affect the above enhancing agents' function, and it may be any sequence.

Figure 5A:
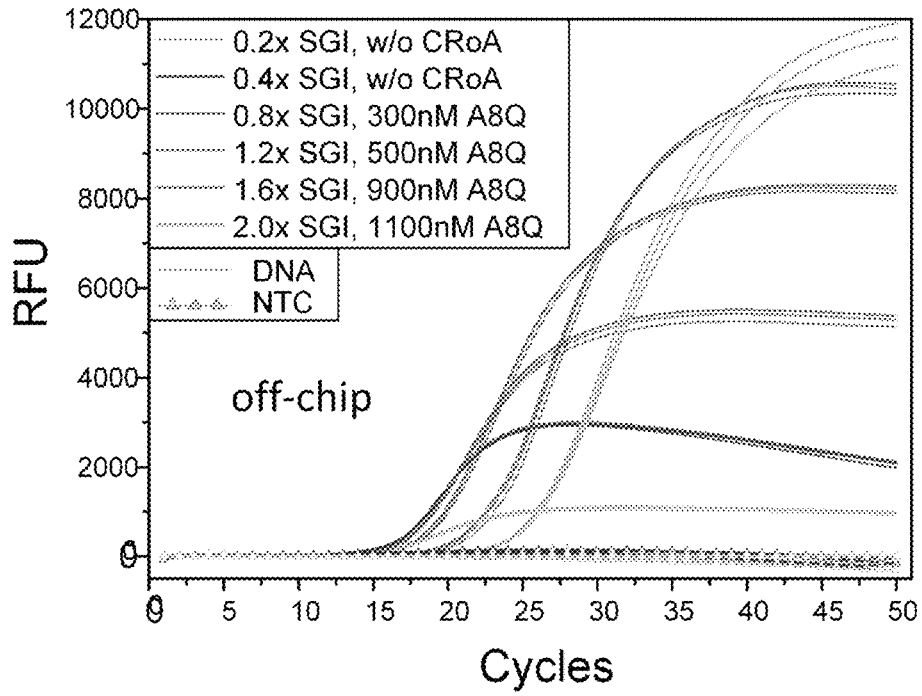
FIG. 5A and FIG. 5B shows off-chip PCR amplification results at different SGI concentrations (0.8×~2.0×) after optimization of the enhancing agent (FIG. 5A) and corresponding on-chip PCR amplification results (FIG. 5B), wherein enhancing agent-free samples in the cases of 0.2×SGI and 0.4×SGI act as control groups.

(e) The Above Enhancing Agents can Increase an Upper Concentration Limit of SGI that can be Used in PCR From the above experimental results, we find that on the premise of successful amplification, the higher the SGI concentration used in PCR, the stronger a terminal fluorescent signal is. In order to explore the upper concentration limit of SGI used in PCR, we further optimized the use of the above enhancing agents at different SGI concentrations (0.8×~2.0×), then found out the A8Q concentration required for the best amplification effect at each SGI concentration, and summarize corresponding amplification curves in FIG. 5A. FIG. 5A also contains amplification results of samples not containing the above enhancing agents at 0.2×SGI and 0.4×SGI, as control groups. Through this series of experiments, it can be seen that SGI with a concentration of up to 1.2× is used in PCR, without inhibiting the amplification efficiency, and the terminal fluorescence intensity is three times that at 0.4×SGI, and 8 times that at 0.2×SGI. When the concentration of SGI is increased to 1.6× and 2.0×, although the inhibition to amplification cannot be avoided, causing delay of the Cq value, the terminal fluorescence intensity thereof is still further increased. Therefore, by introducing the above enhancing agents into the nucleic acid amplification reaction solution, the usable upper concentration limit of SGI can be increased to 2.0×, and the intensity of the amplification signal is multiplied.

Figure 5B:
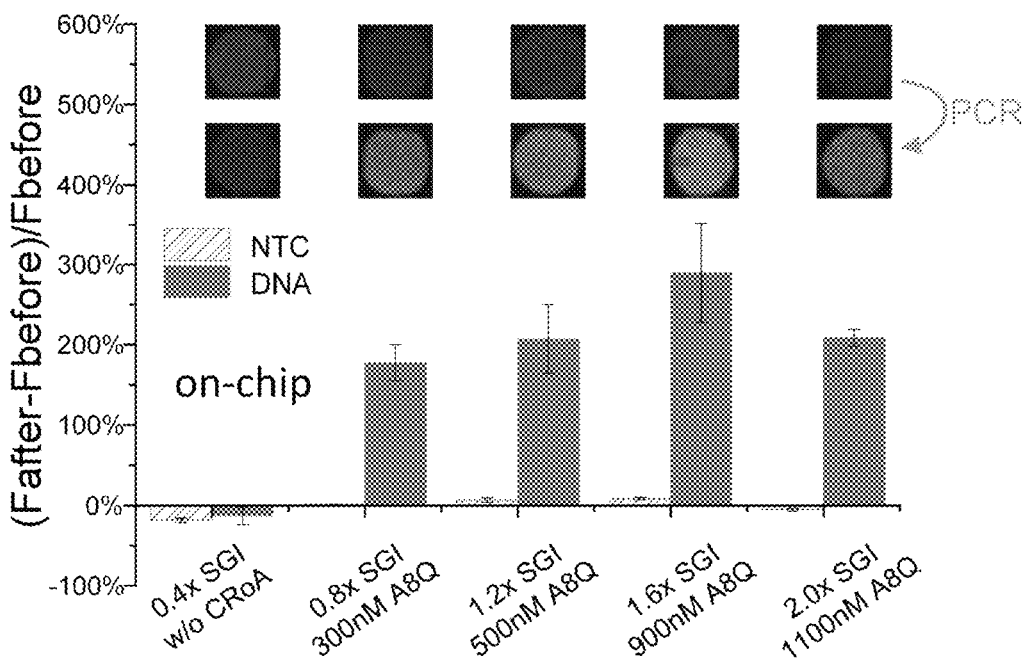

In addition, we applied relatively optimized reaction conditions of off-chip PCR to the digital microfluidic chip, and obtained corresponding on-chip PCR amplification results, as shown in FIG. 5B. Compared with the control groups not containing the above enhancing agents at 0.2× SGI and 0.4×SGI, samples containing different concentrations of A8Q have enhanced on-chip PCR amplification signals under the condition of 0.8×~2.0×SGI.

(f) Effects of the Above Enhancing Agents on Other Nucleic Acid Fluorescent Dyes The above experiments prove the above enhancing agents' function of enhancing the PCR system based on the nucleic acid dye SGI. In order to verify effectiveness of the above enhancing agents on PCR systems based on other nucleic acid dyes, we tested enhancement effects of the above enhancing agents on off-chip PCR and on-chip PCR in PCR systems containing Sytox Green and EvaGreen, respectively.

Figure 6A:
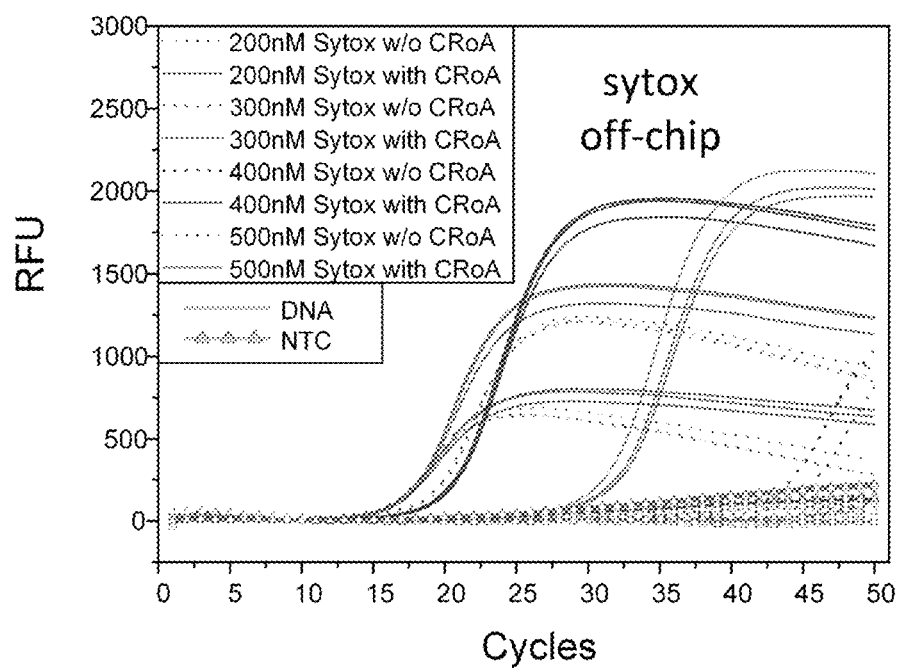
FIG. 6A-FIG. 6D show enhancement effects of the enhancing agent on PCR system based on other nucleic acid dyes (Sytox Green, EvaGreen).
Figure 6B:
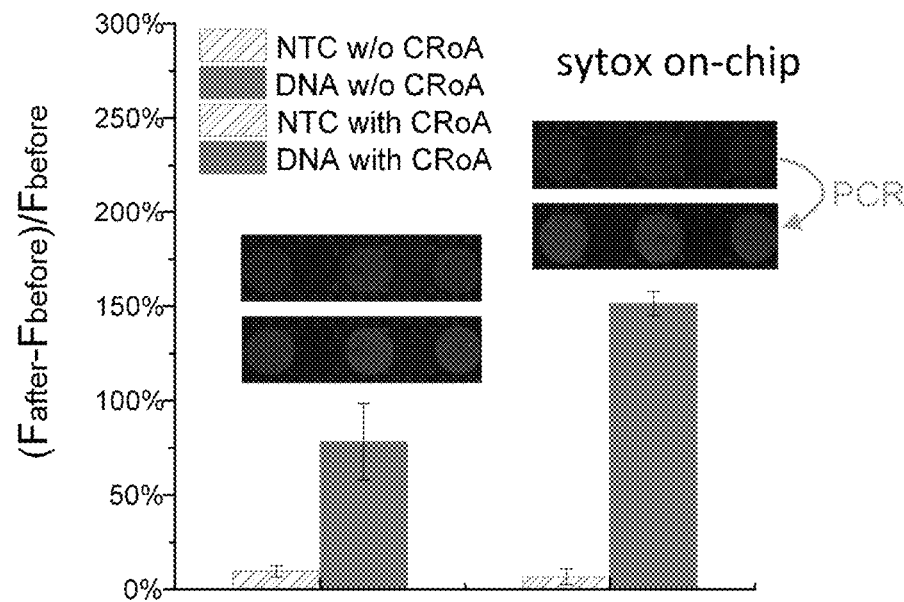
Figure 6C:
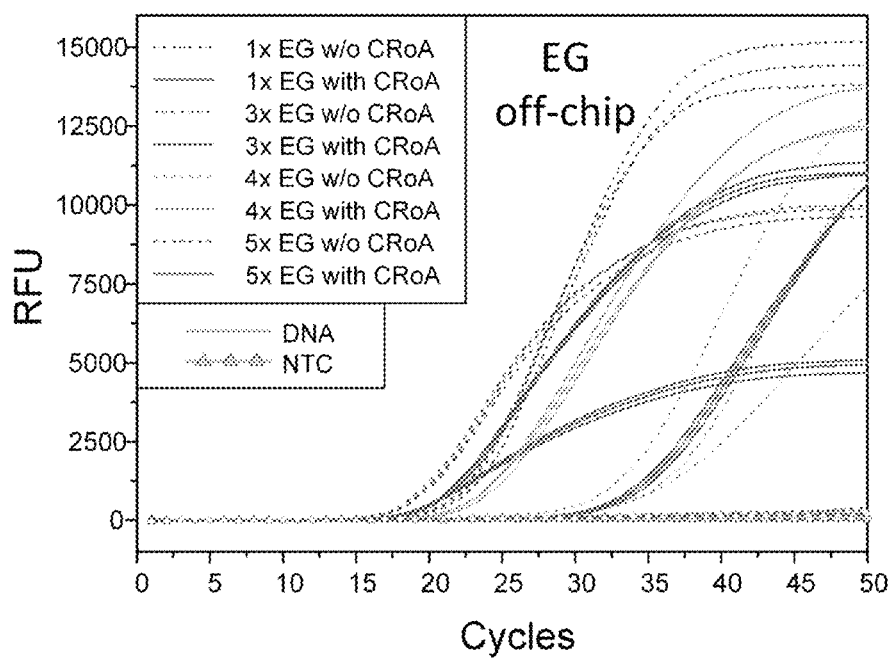
Figure 6D:
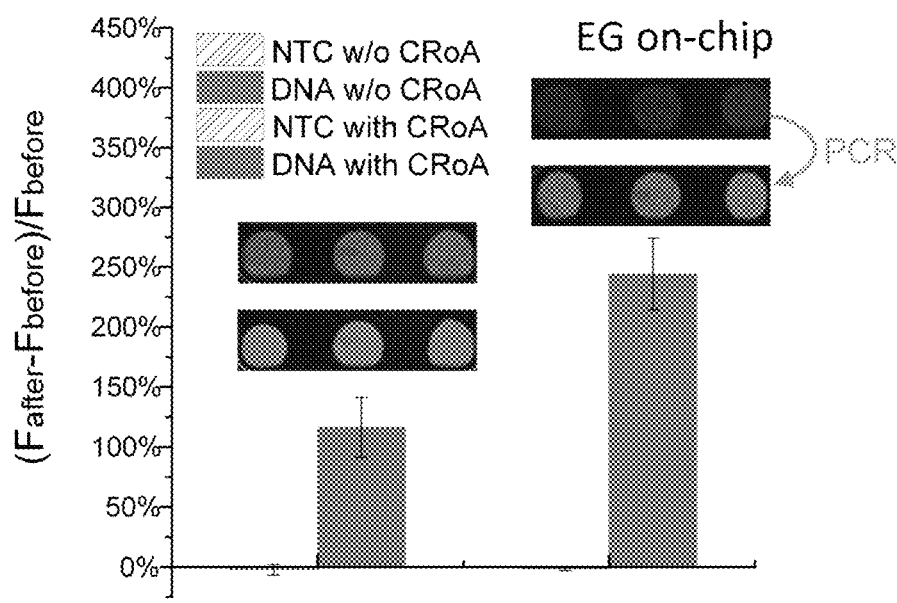

As shown in FIG. 6A, Sytox Green exhibits inhibition to amplification, similar to SGI, at concentrations greater than or equal to 400 nM. The introduction of the above enhancing agents reduces such inhibition. In addition, on-chip PCR results in FIG. 6B show that the above enhancing agents can enhance the Sytox signal of on-chip PCR, and the intensity of change in on-chip PCR amplification signal of the samples containing the above enhancing agents is twice that of the samples not containing the above enhancing agents On the other hand, as EvaGreen does not inhibit amplification at the recommended 1× concentration, we tested the influence of introducing the above enhancing agents on the amplification results at a higher concentration (3×~5×) of EvaGreen. As shown in FIG. 6C, when the samples do not contain the above enhancing agents, 4× EvaGreen starts to inhibit amplification, causing the Cq value to be delayed by more than 10 cycles, and 5× EvaGreen results in failure of amplification. After the above enhancing agents are introduced into the reaction solution, the inhibition of 4× EvaGreen to PCR is weakened, the Cq value is delayed by less than 2 cycles, and the amplification is also successful at 5× EvaGreen. In on-chip PCR, the introduction of the above enhancing agents also amplifies the change in the EvaGreen fluorescence signal by more than one time after amplification.

The above experimental results fully demonstrate that the enhancing agents provided in Examples 1-7 of the present disclosure are effective not only for enhancing the SGI-based PCR system, but also for PCR systems based on other nucleic acid dyes. The enhancing effects of the enhancing agents provided in Examples 1-7, as broad-spectrum PCR enhancing agents, on off-chip PCR and on-chip PCR are confirmed in the above experimental examples.

Experimental Example 2

Verify the function of the enhancing agents in the examples of the present disclosure in loop-mediated isothermal amplification (LAMP)

To test the effectiveness of the enhancing agents in the examples of the present disclosure in nucleic acid amplification reaction systems other than PCR, we took *Trypanosoma brucei* nucleic acid as a template to perform loop-mediated isothermal amplification (LAMP) in off-chip manner, to test influence of CRoA enhancing agent on the amplification reaction.

Materials:

The nucleic acid template used in the present experiment was the genomic DNA of *Trypanosoma brucei*.

Primers used to amplify the gene sequence were as follows:

```
Upstream primer sequence (FP):
                                        (SEQ ID NO. 14)
5'CTGTCCGGTGATGTGGAAC3'

Upstream primer sequence (BP):
                                        (SEQ ID NO. 15)
5'CGTGCCTTCGTGAGAGTTTC3';

Upstream internal primer sequence (FIP):
                                        (SEQ ID NO. 16)
5'GGAATACAGCAGATGGGGCGAGGCCAATTGGCATCTTTGGGA3';

Downstream internal primer sequence (BIP):
                                        (SEQ ID NO. 17)
5'AAGGGAGACTCTGCCACAGTCGTCAGCCATCACCGTAGAGC3';

Loop upstream primer sequence (LFP):
                                        (SEQ ID NO. 18)
5'GCCTCCCACCCTGGACTC3';

Loop downstream primer sequence (LBP):
                                        (SEQ ID NO. 19)
5'AGACCGATAGCATCTCAG3'.
```

Method:

In the present experiment, a volume of a real-time fluorescent LAMP reaction solution was 10 μL, containing 1×LAMP buffer (NEB, USA), 6 mM MgCl$_2$ (Invitrogen, USA), 1.4 mM dNTP (Invitrogen, USA), 400 nM upstream primer and 400 nM downstream primer, 1600 nM upstream internal primer and 1600 nM downstream internal primer, 800 nM loop upstream primer and 800 nM loop downstream primer, 16 units of Bst polymerase (Invitrogen, USA), different concentrations (0.4×, 0.8× or 1.2×) of SGI and A8Q (at 0.4×SGI, 100 nM A8Q was used; at 0.8×SGI, 300 nM A8Q was used; at 1.2×SGI, 500 nM A8Q was used.). For the positive samples, 1×10$^5$ copies of nucleic acid template were added to the reaction solution, and ultrapure water was added to the negative sample reaction solution to replace the template. The off-chip reaction was performed on a Biorad CFX 96 real-time fluorescent amplifier at 65° C. for 60 min, and a following melting analysis procedure was: from 35° C. to 95° C., residing at each temperature for 2 s at an interval of 1° C. Three parallel samples were made for each off-chip LAMP reaction.

Figure 7:
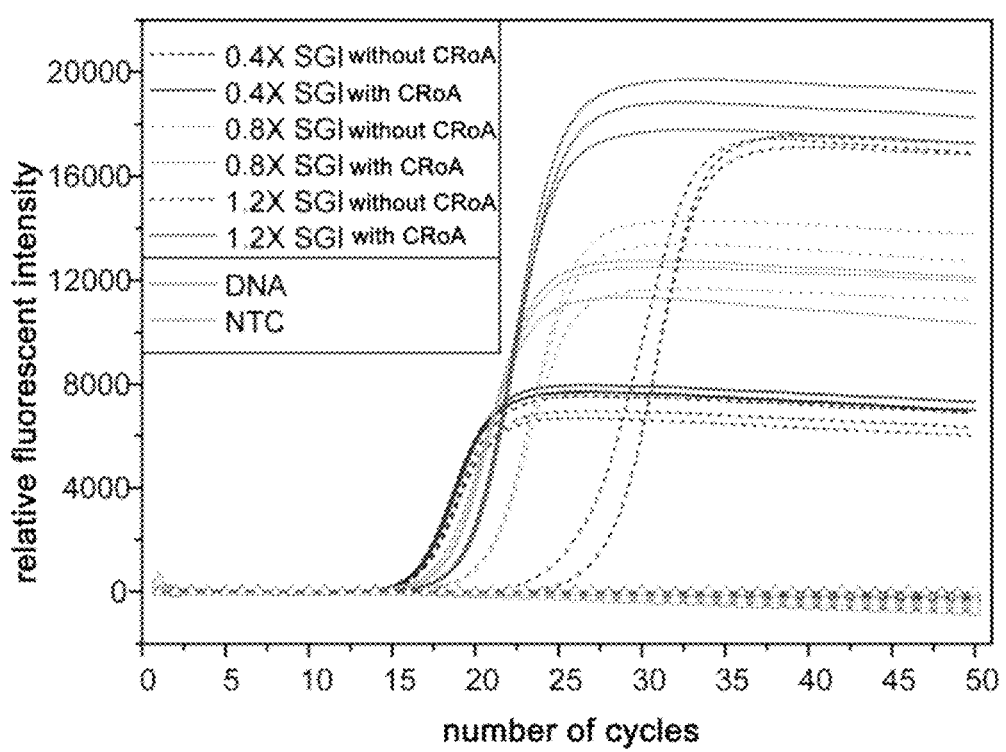
FIG. 7 shows enhancement effect of the enhancing agent on LAMP amplification system. Amplification curves of CRoA-free samples and of CRoA-containing samples are compared when SGI concentrations are 0.4×, 0.8×, and 1.2× respectively, in off-chip LAMP. At 0.4×SGI, 100 nM A8Q is used for the CRoA-containing samples; in the case of 0.8×SGI, 300 nM A8Q is used for the CRoA-containing samples; in the case of 1.2×SGI, 500 nM A8Q is used for the CRoA-containing samples.

Results:

As shown in FIG. 7, in the LAMP amplification system, high-concentration SGI also inhibits amplification. Compared with 0.4×SGI, the Cq value has a delay of 3 cycles when the SGI concentration is increased to 0.8×; the Cq value has a delay of nearly 10 cycles when the SGI concentration continues to be increased to 1.2×.

The effects of the enhancing agents provided in the examples of the present disclosure are also effective in the nucleic acid amplification system such as LAMP. When the SGI concentration is 0.4×, curves of samples not containing CRoA (A8Q) and of samples containing CRoA are substantially consistent; as the SGI concentration is gradually increased, the presence of CRoA in the reaction solution makes the SGI's inhibition to the amplification reaction almost disappear. At 0.8×SGI, the Cq value is almost not delayed compared with that at 0.4×SGI; at 1.2×SGI, the Cq value is only delayed within 2 cycles compared with that at 0.4×SGI, while at the same time, the fluorescence intensity during the amplification reaction plateau can be more than 2 times that at 0.4×SGI.

To sum up, we have verified the enhancement effects of the enhancing agents provided in the examples of the present disclosure on off-chip PCR, on-chip PCR and LAMP. By adjusting the concentration of free dye molecules in the solution, the enhancing agents provided in the examples of the present disclosure are capable of reducing the attenuation effect of high-concentration dye to amplification efficiency. At the same time, on the digital microfluidic chip, the enhancing agents provided in the examples of the disclosure, as temporary binding sites of the dye molecules, can avoid damage of the nucleic acid dye, thereby enhancing the amplification signal of on-chip PCR. In addition, the gel electrophoresis results in FIG. 2F predict that the enhancing agents provided in the examples of the present disclosure further may be capable of reducing non-specific amplification products and improving PCR specificity. As the high-concentration SGI will stabilize the non-specific binding of the primer and the nucleic acid template, the introduction of the enhancing agents provided in the examples of the present disclosure to reduce free SGI molecules in the solution is likely to improve the amplification specificity. Researchers have also explored a variety of methods for nucleic acid dye to enhance PCR. For example, Kong et al. (Kong, J. E., Wei, Q., Tseng, D., Zhang, J., Pan, E., Lewinski, M., Garner, O. B., Ozcan, A. and Di Carlo, D. (2017) Highly Stable and Sensitive Nucleic Acid Amplification and Cell-Phone-Based Readout. ACS nano, 11, 2934-2943.) found that HNB can interact with EvaGreen to improve the amplification efficiency while reducing background fluorescence. In addition, Nath et al. (Nath, K., Sarosy, J. W., Hahn, J. and Di Como, C. J. (2000) Effects of ethidium bromide and SYBR Green I on different polymerase chain reaction systems. J Biochem Biophys Methods, 42, 15-29.) found that magnesium chloride can partially reverse the inhibitory effects of EtBr and SGI on amplification. However, the enhancing functions of these PCR additives are all affected by ion concentration, and the PCR-enhancing efficacy thereof can be regulated to a limited extent only by varying the concentration of these additives. In contrast, the mechanism of action of the enhancing agents provided in the examples of the present disclosure is that the attraction of the double-stranded stem structure to the dye molecules is not influenced by the ion concentration, and the effect thereof not only can be adjusted by the concentration of the enhancing agents provided in the examples of the present disclosure, but also can be flexibly adjusted through fine adjustment of the structures of the enhancing agents provided in the examples of the present disclosure.

In addition to being capable of enhancing off-chip PCR and on-chip PCR, the enhancing agents provided in the examples of the present disclosure can also enhance LAMP, and these enhancing agents also have potentials for application in other methods such as HRM. Due to the inhibition of high-concentration fluorescent dye to PCR, fluorescent dye can only be used in a low concentration range, and conventional fluorescent dyes are not suitable for use in methods requiring high sensitivity signals such as HRM. However, the enhancing agents provided in the examples of the present disclosure increase the usable upper concentration limit of fluorescent dye such as SGI, such that the signal intensity and resolution of SGI are multiplied, giving the fluorescent dye the potential of being applied to HRM.

The mechanism of action of the enhancing agents provided in the examples of the present disclosure, i.e. temporarily storing the nucleic acid dye molecules and releasing them as desired along with the amplification, is a simple but effective method for enhancing the nucleic acid amplification reaction. By introducing the above enhancing agents provided in the examples of the present disclosure into the nucleic acid amplification reaction solution, we eliminated the disadvantages of double-stranded DNA fluorescent dye, allowing them to be better applied to conventional PCR, off-chip PCR, microfluidic control chip-based on-chip PCR, LAMP and other nucleic acid amplification reactions.

The above-mentioned are merely for preferred examples of the present disclosure but are not used to limit the present disclosure. For one skilled in the art, various modifications and changes may be made to the present disclosure. Any amendments, equivalent replacements, improvements, and so on, within the spirit and principle of the present disclosure, should be covered within the scope of protection of the present disclosure.

What is claimed is:

1. An enhancing agent for enhancing nucleic acid amplification reaction, wherein the enhancing agent is applicable to nucleic acid amplification reaction containing fluorescent dye(s), the fluorescent dye(s) is capable of binding to double-stranded amplification products of the nucleic acid amplification reaction;

the enhancing agent has a domain and a quenching group, wherein the domain is capable of binding to the fluorescent dye(s), and the quenching group is used for quenching fluorescence emitted by the fluorescent dye(s) bound to the domain, a binding affinity of the domain to the fluorescent dye(s) is lower than a binding affinity of a target amplification product of the nucleic acid amplification reaction to the fluorescent dye(s), wherein the fluorescent dye(s) is not covalently attached to the enhancing agent, and the enhancing agent does not comprise a fluorophore moiety attached thereto, wherein the enhancing agent is a DNA nucleic acid molecule, and a linearized base sequence of the DNA nucleic acid molecule is any one of SEQ ID NOs. 1-7, wherein the DNA nucleic acid molecule has at least one stem structure region, the stem structure region is composed of a 5'-end stem region and a 3'-end stem region bound to each other through base complementary pairing to form a double-stranded structure region, the quenching group is located at the 5' end of the 5'-end stem region or the 3' end of the 3'-end stem region, and the quenching group is any one selected from the group consisting of 2,5-bis(2-methyl-2-propanyl)-1,4-benzenediol, N-methyl-N-[4-[2-methoxy-5-methyl-4-(2-nitro-4-methylphenylazo)phenylazo]-phenyl]-4-aminobutyric acid, N-methyl-N-[4-[2,5-dimethoxy-4-(4-nitrophenylazo)phenylazo]phenyl]-4-amin-obutyric acid, 6-[[4-(dimethylamino)phenyl]diazenyl]-N,N-diethyl-10-phenylacridin-10-ium-3-amine, 4-[[4-(dimethylamino)phenyl]diazenyl]benzoic acid and carboxytetramethylrhodamine.

2. The enhancing agent according to claim 1, wherein the domain capable of binding to the fluorescent dye(s) is the double-stranded structure region; the quenching group is located at 5' end or 3' end of the double-stranded structure region.

3. The enhancing agent according claim 2, wherein the fluorescent dye(s) is any one selected from the group consisting of N,N-dimethyl-N'-[4-[(E)-(3-methyl-1,3-benzothiazol-2-ylidene)methyl]-1-phenylquinolin-1-ium-2-yl]-N'-propylpropane-1,3-diamine, 6-[3,6-bis(dimethylamino)acridin-10-ium-10-yl]-N-[2-[2-[6-[3,6-bis(dimethylamino)acridin-10-ium-10-yl]hexanoylamino]ethoxy]ethyl]hexanamide, ethidium bromide, 3,5-dichloro-N-(4-methoxy-2-nitrophenyl)benzamide, (Z)-4-((3-methylbenzo[d]thiazol-2 (3H)-ylidene)methyl)-1-propylquinolin-1-ium 4-methylbenzenesulfonate, 6-[3,6-bis(dimethylamino)acridin-10-ium-10-yl]-N-[3-[2-[2-[3-[6-[3,6-bis(dimethylamino)acridin-10-ium-10-yl]hexanoylamino]propoxy]ethoxy]ethoxy]propyl]hexanamide diiodide, 6-(3,8-diamino-6-phenylphenanthridin-5-ium-5-yl)-N-[3-[2-[2-[3-[6-(3,8-diamino-6-phenylphenanthridin-5-ium-5-yl)hexanoylamino]propoxy]ethoxy]ethoxy]propyl]hexanamide diiodide, 2-(4-carbatnitnidoylphenyl)-1H-indole-6-carboxitnidamide and 1-methyl-4-[(3-methyl-2 (3H)-benzothiazolylidene)methyl]quinolinium p-tosylate.

4. A nucleic acid amplification reaction solution, comprising the enhancing agent according to claim 1.

* * * * *

SEQUENCE LISTING

```
<160> NUMBER OF SEQ ID NOS: 22

<210> SEQ ID NO 1
<211> LENGTH: 14
<212> TYPE: DNA
<213> ORGANISM: Artificial Sequence
<220> FEATURE:
<223> OTHER INFORMATION: Enhancing agent, with 3' end labeled by BHQ2
```

<400> SEQUENCE: 1
ccaaaaaaaa aagg                                                        14

<210> SEQ ID NO 2
<211> LENGTH: 22
<212> TYPE: DNA
<213> ORGANISM: Artificial Sequence
<220> FEATURE:
<223> OTHER INFORMATION: Enhancing agent, with 3' end labeled by BHQ2

<400> SEQUENCE: 2
ccgcaaaaaa aaaaaaaagc gg                                               22

<210> SEQ ID NO 3
<211> LENGTH: 26
<212> TYPE: DNA
<213> ORGANISM: Artificial Sequence
<220> FEATURE:
<223> OTHER INFORMATION: Enhancing agent, with 3' end labeled by BHQ2

<400> SEQUENCE: 3
ccgctgaaaa aaaaaaaaaa cagcgg                                           26

<210> SEQ ID NO 4
<211> LENGTH: 30
<212> TYPE: DNA
<213> ORGANISM: Artificial Sequence
<220> FEATURE:
<223> OTHER INFORMATION: Enhancing agent, with 3' end labeled by BHQ2

<400> SEQUENCE: 4
ccgctgcgaa aaaaaaaaaa aacgcagcgg                                       30

<210> SEQ ID NO 5
<211> LENGTH: 34
<212> TYPE: DNA
<213> ORGANISM: Artificial Sequence
<220> FEATURE:
<223> OTHER INFORMATION: Enhancing agent, with 3' end labeled by BHQ2

<400> SEQUENCE: 5
ccgctgcgcg aaaaaaaaaa aaaacgcgca gcgg                                  34

<210> SEQ ID NO 6
<211> LENGTH: 44
<212> TYPE: DNA
<213> ORGANISM: Artificial Sequence
<220> FEATURE:
<223> OTHER INFORMATION: Enhancing agent, with 3' end labeled by BHQ2

<400> SEQUENCE: 6
cgtgccgctg gtcgcaaaaa aaaaaaaaag cgaccagcgg cacg                       44

<210> SEQ ID NO 7
<211> LENGTH: 23
<212> TYPE: DNA
<213> ORGANISM: Artificial Sequence
<220> FEATURE:
<223> OTHER INFORMATION: Enhancing agent, with 3' end labeled by BHQ2
      and 5' end labeled by CY5

<400> SEQUENCE: 7
ccggactctg cttgttatgc cgg                                              23

```
<210> SEQ ID NO 8
<211> LENGTH: 54
<212> TYPE: DNA
<213> ORGANISM: Artificial Sequence
<220> FEATURE:
<223> OTHER INFORMATION: Comparative enhancing agent, with 3' end
      labeled by BHQ2

<400> SEQUENCE: 8
cgtgccgctg gttcgctggc aaaaaaaaaa aaaagccagc gaaccagcgg cacg        54

<210> SEQ ID NO 9
<211> LENGTH: 22
<212> TYPE: DNA
<213> ORGANISM: Artificial Sequence
<220> FEATURE:
<223> OTHER INFORMATION: Comparative enhancing agent, with 3' end
      labeled by C3 spacer

<400> SEQUENCE: 9
ccgcaaaaaa aaaaaaaagc gg                                           22

<210> SEQ ID NO 10
<211> LENGTH: 10
<212> TYPE: DNA
<213> ORGANISM: Artificial Sequence
<220> FEATURE:
<223> OTHER INFORMATION: Comparative enhancing agent, with 3' end
      labeled by BHQ2

<400> SEQUENCE: 10
aaaaaaaaaa                                                         10

<210> SEQ ID NO 11
<211> LENGTH: 311
<212> TYPE: DNA
<213> ORGANISM: Homo sapiens

<400> SEQUENCE: 11
cgaggtcatt gaatacgcac ggctccgggg tatccgtgtg cttgcagagt ttgacactcc   60
tggccacact ttgtcctggg gaccaggtaa gaatgatgtc tgggaccaga gggactctgc  120
ttgttatgct cagagtgaag cttcagggca ctggctcatg gaagtggcat atcccagctt  180
ggtccttaga agaatgtttt ccatcgactt cttccacctg ggaatttaga taggaagaac  240
tcactttgga caatggaggc tgcttcttac tattaaaata tgtactgtta gactatgtaa  300
gggcacagcg c                                                      311

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gaatgatgtc tgggaccaga                                              20

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
```

```
gaccaagctg ggatatgcc                                                    19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
ctgtccggtg atgtggaac                                                    19

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cgtgccttcg tgagagtttc                                                   20

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
ggaatacagc agatggggcg aggccaattg gcatctttgg ga                          42

<210> SEQ ID NO 17
<211> LENGTH: 41
<212> TYPE: DNA
<213> ORGANISM: Artificial Sequence
<220> FEATURE:
<223> OTHER INFORMATION: Primer

<400> SEQUENCE: 17
aagggagact ctgccacagt cgtcagccat caccgtagag c                           41

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
gcctcccacc ctggactc                                                     18

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
agaccgatag catctcag                                                     18

<210> SEQ ID NO 20
<211> LENGTH: 10
<212> TYPE: DNA
```

```
<213> ORGANISM: Artificial Sequence
<220> FEATURE:
<223> OTHER INFORMATION: 5' stem region

<400> SEQUENCE: 20
ccgctgcgcg                                                                  10

<210> SEQ ID NO 21
<211> LENGTH: 15
<212> TYPE: DNA
<213> ORGANISM: Artificial Sequence
<220> FEATURE:
<223> OTHER INFORMATION: 5' stem region

<400> SEQUENCE: 21
cgtgccgctg gtcgc                                                            15

<210> SEQ ID NO 22
<211> LENGTH: 14
<212> TYPE: DNA
<213> ORGANISM: Artificial Sequence
<220> FEATURE:
<223> OTHER INFORMATION: PolyA

<400> SEQUENCE: 22
aaaaaaaaaa aaaa                                                             14
```